US009815843B2

(12) United States Patent
Pak et al.

(10) Patent No.: US 9,815,843 B2
(45) Date of Patent: Nov. 14, 2017

(54) COMPOUND, PHOTOSENSITIVE RESIN COMPOSITION COMPRISING THE SAME, AND COLOR FILTER

(71) Applicant: Samsung SDI Co., Ltd., Yongin-si (KR)

(72) Inventors: Chae Won Pak, Suwon-si (KR); Hye Won Seo, Suwon-si (KR); Myoung Youp Shin, Suwon-si (KR); Eui Soo Jeong, Suwon-si (KR); Seung Jib Choi, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 0 days.

(21) Appl. No.: 15/266,543

(22) Filed: Sep. 15, 2016

(65) Prior Publication Data

US 2017/0107224 A1    Apr. 20, 2017

(30) Foreign Application Priority Data

Oct. 16, 2015 (KR) ........................ 10-2015-0144786

(51) Int. Cl.

| | |
|---|---|
| *G02B 5/20* | (2006.01) |
| *C09B 47/04* | (2006.01) |
| *C07D 487/22* | (2006.01) |
| *C09B 47/067* | (2006.01) |
| *G02B 5/22* | (2006.01) |
| *G03F 7/00* | (2006.01) |
| *G03F 7/033* | (2006.01) |

(52) U.S. Cl.
CPC ........ *C07D 487/22* (2013.01); *C09B 47/0671* (2013.01); *C09B 47/0675* (2013.01); *G02B 5/223* (2013.01); *G03F 7/0007* (2013.01); *G03F 7/033* (2013.01)

(58) Field of Classification Search
CPC ........ G03F 7/0007; G03F 7/033; G03F 7/028; G02B 5/223; C07D 487/22; C07B 47/04; C07B 47/10; C07B 47/18; C07B 47/061; C07B 47/0671; C07B 47/063; C07B 47/0675
USPC ....... 430/7, 270.1, 281.1; 540/136, 137, 140
See application file for complete search history.

(56) References Cited

U.S. PATENT DOCUMENTS

| | | | |
|---|---|---|---|
| 5,998,091 A | 12/1999 | Suzuki | |
| 6,033,813 A | 3/2000 | Endo et al. | |
| 6,726,755 B2 | 4/2004 | Titterington et al. | |
| 6,733,935 B2 | 5/2004 | Kishimoto et al. | |
| 7,517,619 B2 | 4/2009 | Hosaka et al. | |
| 7,781,026 B2 | 8/2010 | Banning | |
| 2005/0208394 A1 | 9/2005 | Suzuki | |
| 2007/0179285 A1 | 8/2007 | Berneth et al. | |
| 2008/0095950 A1 | 4/2008 | Hall-Goulle et al. | |
| 2009/0189086 A1 | 7/2009 | Gessner et al. | |
| 2012/0267612 A1 | 10/2012 | Xia et al. | |
| 2015/0053900 A1* | 2/2015 | Kim ........................ G02B 1/04 252/586 |
| 2015/0192699 A1 | 7/2015 | Choi et al. | |
| 2015/0322077 A1* | 11/2015 | Shin ........................ C09B 47/04 430/5 |
| 2015/0331316 A1* | 11/2015 | Choi ................... C09B 47/0671 252/586 |

FOREIGN PATENT DOCUMENTS

| | | |
|---|---|---|
| CN | 101421236 A | 4/2009 |
| JP | 06-041458 A | 2/1994 |
| JP | 07-140654 A | 6/1995 |
| JP | 10-254133 A | 9/1998 |
| JP | 2005-265994 A | 9/2005 |
| JP | 2010-077408 A | 4/2010 |
| JP | 2013-241563 A | 12/2013 |
| JP | 2014-028950 A | 2/2014 |
| JP | 2015-086268 A | 5/2015 |
| KR | 10-1999-0007097 A | 1/1999 |
| KR | 10-2002-0015650 A | 2/2002 |
| KR | 10-2005-0020653 A | 3/2005 |

(Continued)

OTHER PUBLICATIONS

Hu et al. "Reverse saturable absorption of copper phthalocyanines in toluene and sol-gel tetraethyl orthosilicate/polyvinyl butyral hybrid film"; Dyes and Pigments 62, pp. 11-19 (2004).*

(Continued)

*Primary Examiner* — John A McPherson
(74) *Attorney, Agent, or Firm* — Additon, Higgins & Pendleton, P.A.

(57) ABSTRACT

A compound represented by Chemical Formula 1 wherein each substituent is the same as defined in the specification, a photosensitive resin composition including the same, and a color filter manufactured using the photosensitive resin composition are provided.

[Chemical Formula 1]

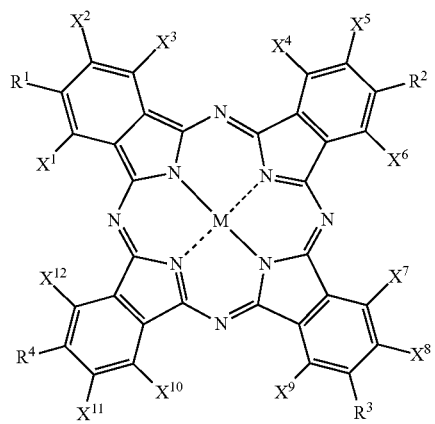

19 Claims, No Drawings

(56) References Cited

FOREIGN PATENT DOCUMENTS

| | | |
|---|---|---|
| KR | 10-2009-0106226 A | 10/2009 |
| KR | 10-2010-0078845 A | 7/2010 |
| KR | 10-2010-0080142 A | 7/2010 |
| KR | 10-2014-0006871 A | 1/2014 |
| KR | 10-2015-0083384 A | 7/2015 |
| TW | 201508033 A | 3/2015 |

OTHER PUBLICATIONS

Search Report in counterpart Taiwanese Application No. 105129895 dated Mar. 16, 2017, pp. 1.
Snow et al., "Molecular Association and Monolayer Formation of Soluble Phthalocyanine Compounds", J. Am. Chem. Soc., vol. 106, No. 17 (1984) pp. 4706-4711.

* cited by examiner

COMPOUND, PHOTOSENSITIVE RESIN COMPOSITION COMPRISING THE SAME, AND COLOR FILTER

CROSS-REFERENCE TO RELATED APPLICATION

This application claims priority to and the benefit of Korean Patent Application No. 10-2015-0144786 filed in the Korean Intellectual Property Office on Oct. 16, 2015, the entire disclosure of which is incorporated herein by reference.

FIELD

This disclosure relates to a novel compound, a photosensitive resin composition including the same, and a color filter.

BACKGROUND

A color filter manufactured by using a pigment-type photosensitive resin composition can be limited in terms of luminance and contrast ratio caused by pigment particle size. In addition, an imaging sensor device requires a smaller dispersion particle size to form a fine pattern.

Prior attempts to realize a color filter having improved color characteristics such as luminance, contrast ratio and the like have used a dye (with no particles) instead of a pigment to manufacture a photosensitive resin composition. Accordingly, there is a need for an appropriate compound as the dye used to manufacture the photosensitive resin composition.

SUMMARY OF THE INVENTION

One embodiment provides a novel compound.

Another embodiment provides a photosensitive resin composition including the compound.

Yet another embodiment provides a color filter manufactured using the photosensitive resin composition.

One embodiment provides a compound represented by the following Chemical Formula 1:

[Chemical Formula 1]

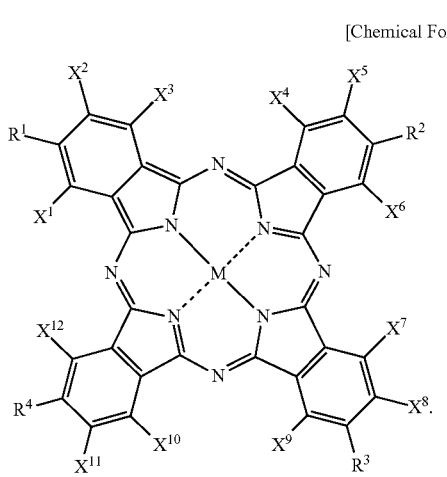

In Chemical Formula 1,

M is Zn or Cu, $X^1$ to $X^{12}$ are the same or different and are each independently a hydrogen atom or a halogen atom, $R^1$ to $R^4$ are the same or different and are each independently a hydrogen atom, a halogen atom, a substituted or unsubstituted C1 to C20 alkyl group, a substituted or unsubstituted C3 to C20 alkoxy group, a substituted or unsubstituted C6 to C20 aryl group, or a substituted or unsubstituted C6 to C20 aryloxy group, provided that at least one of $R^1$ to $R^4$ is represented by Chemical Formula 2,

[Chemical Formula 2]

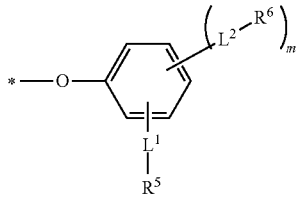

wherein, in Chemical Formula 2, $L^1$ and $L^2$ are the same or different and are each independently a single bond or a substituted or unsubstituted C1 to C10 alkylene group, provided that $L^1$ and $L^2$ are not simultaneously a single bond, $R^5$ and $R^6$ are the same or different and are each independently a substituted or unsubstituted C3 to C20 cycloalkyl group or a substituted or unsubstituted C6 to C20 aryl group, provided that when $L^1$ is a single bond, $R^5$ is a substituted or unsubstituted C3 to C20 cycloalkyl group, and m is an integer of 0 or 1.

Chemical Formula 2 may be represented by the following Chemical Formula 3:

[Chemical Formula 3]

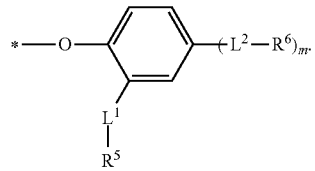

In Chemical Formula 3, $L^1$ is a single bond or a substituted or unsubstituted C1 to C10 alkylene group, $L^2$ is a substituted or unsubstituted C1 to C10 alkylene group, $R^5$ is a substituted or unsubstituted C3 to C20 cycloalkyl group, $R^6$ is a substituted or unsubstituted C6 to C20 aryl group, and m is an integer of 0 or 1.

Chemical Formula 2 may be represented by the following Chemical Formula 3-1 and/or Chemical Formula 3-2:

[Chemical Formula 3-1]

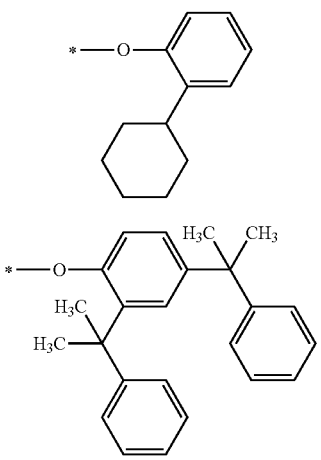

[Chemical Formula 3-2]

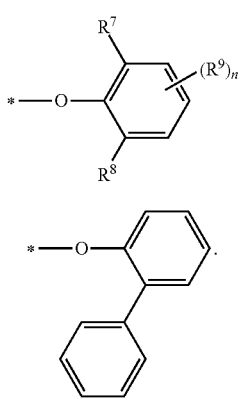

At least two of $R^1$ to $R^4$ may be represented by Chemical Formula 2.

At least three of $R^1$ to $R^4$ may be represented by Chemical Formula 2.

All of $R^1$ to $R^4$ may be represented by Chemical Formula 2.

The substituted or unsubstituted C3 to C20 alkoxy group may be represented by the following Chemical Formula 4:

[Chemical Formula 4]

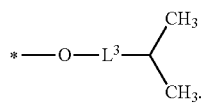

In Chemical Formula 4, $L^3$ is a single bond or a substituted or unsubstituted C1 to C17 alkylene group.

The substituted or unsubstituted C6 to C20 aryloxy group may be represented by the following Chemical Formula 5 and/or Chemical Formula 6:

[Chemical Formula 5]

[Chemical Formula 6]

In Chemical Formula 5, $R^7$ and $R^8$ are the same or different and are each independently a substituted or unsubstituted C1 to C7 alkyl group, $R^9$ is a halogen atom, and n is an integer of 0 or 1.

The compound represented by Chemical Formula 1 may include one or more selected from the following Chemical Formula 7 to Chemical Formula 16:

[Chemical Formula 7]

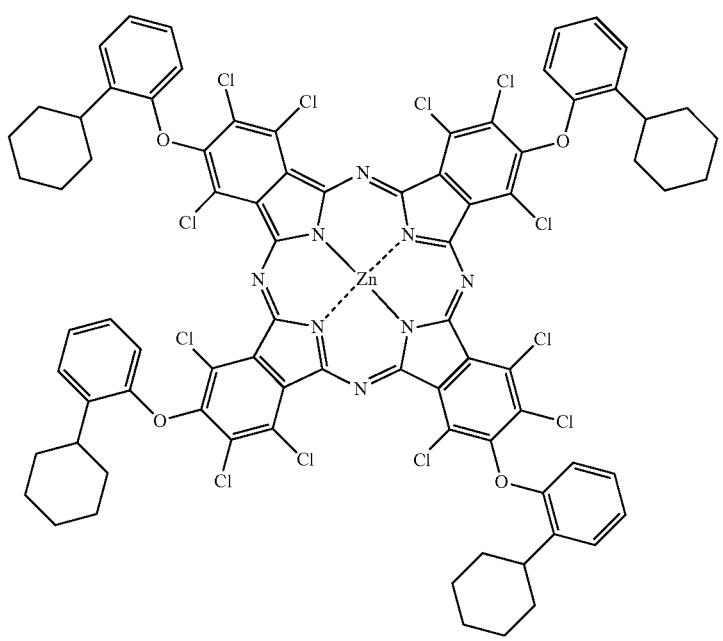

-continued
[Chemical Formula 8]
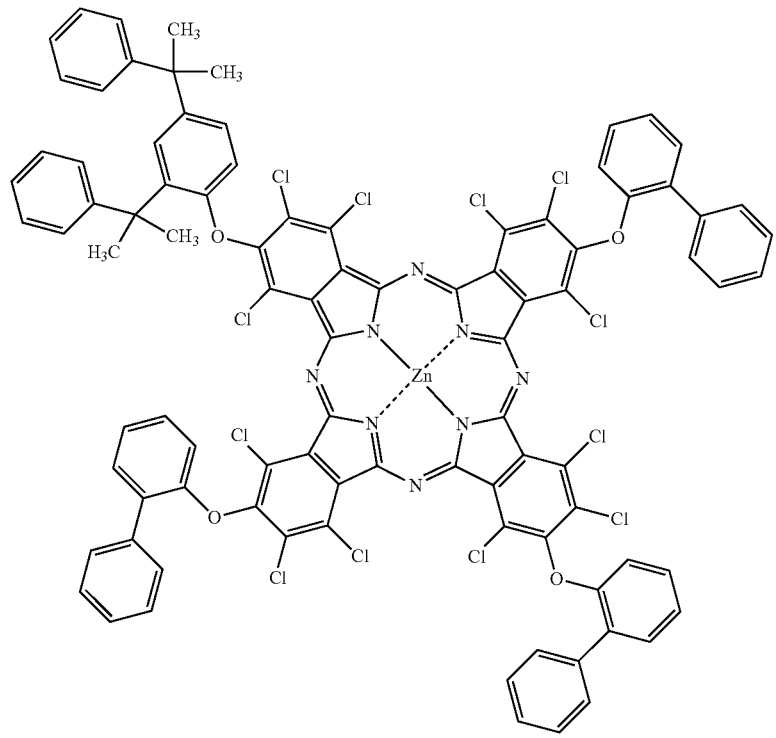
[Chemical Formula 9]
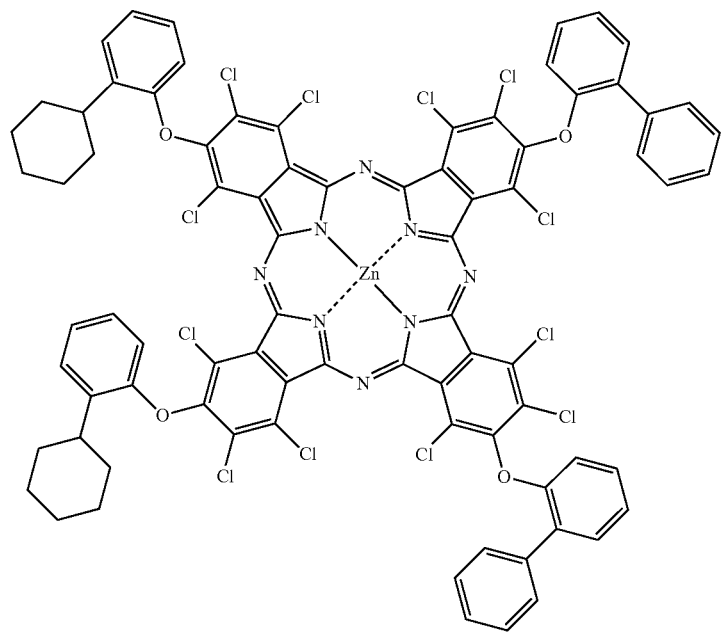

[Chemical Formula 10]
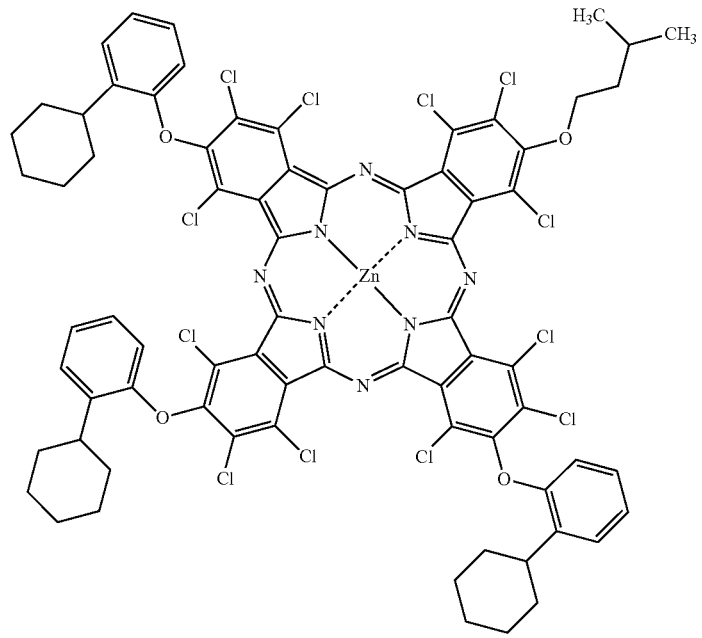
[Chemical Formula 11]
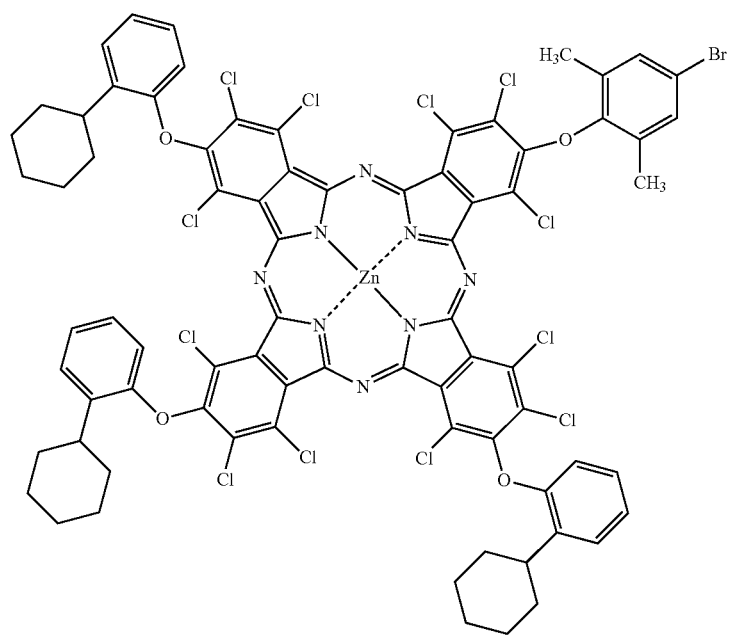

[Chemical Formula 12]
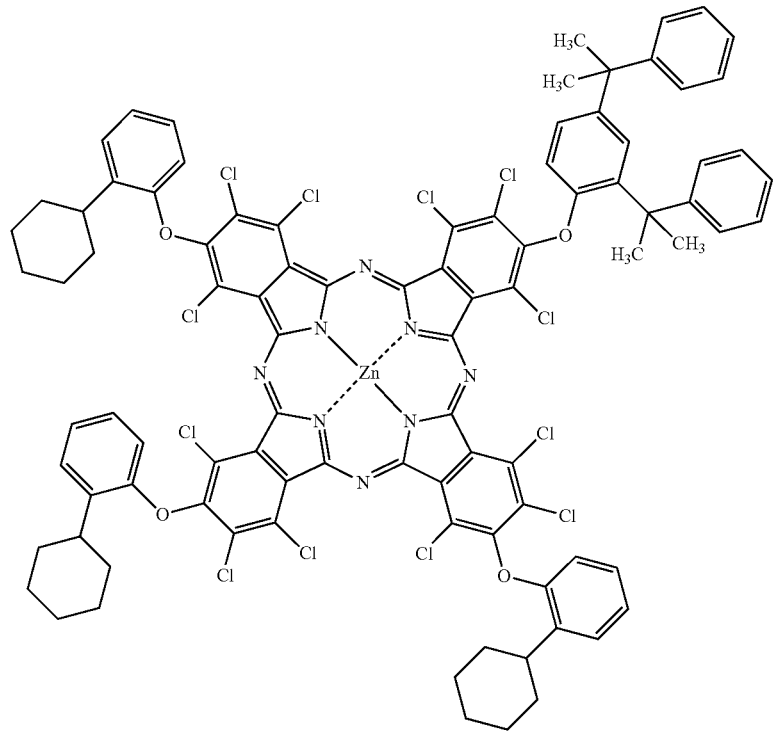
[Chemical Formula 13]
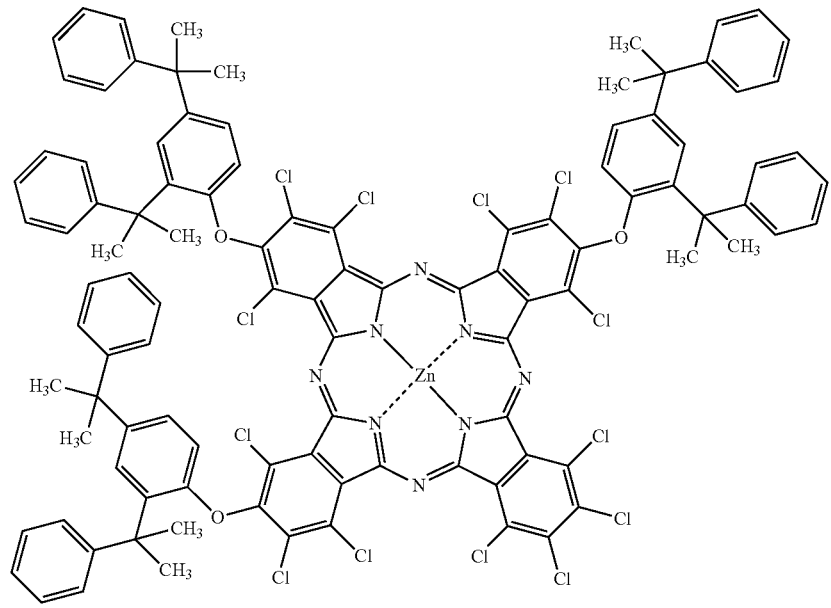

[Chemical Formula 14]
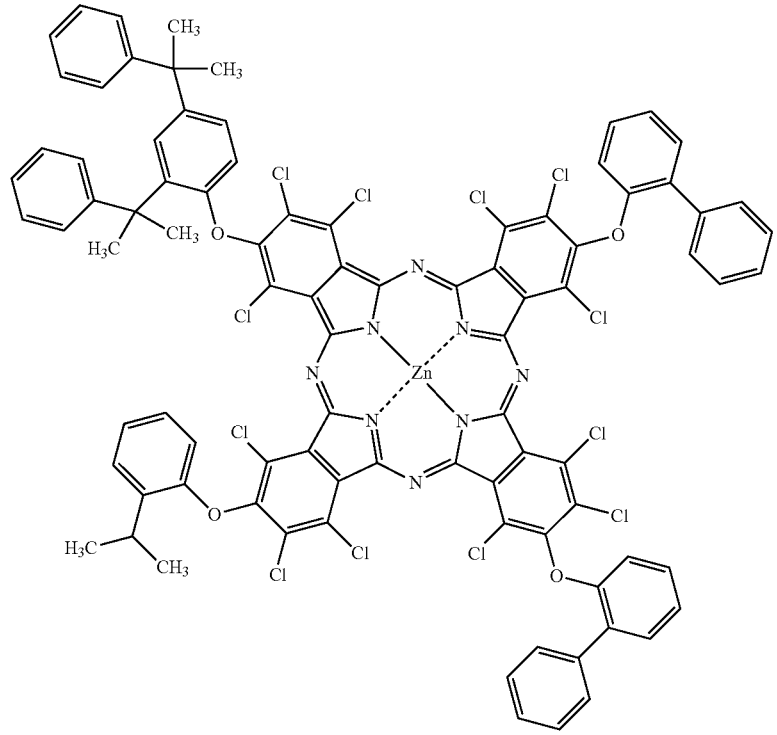
[Chemical Formula 15]
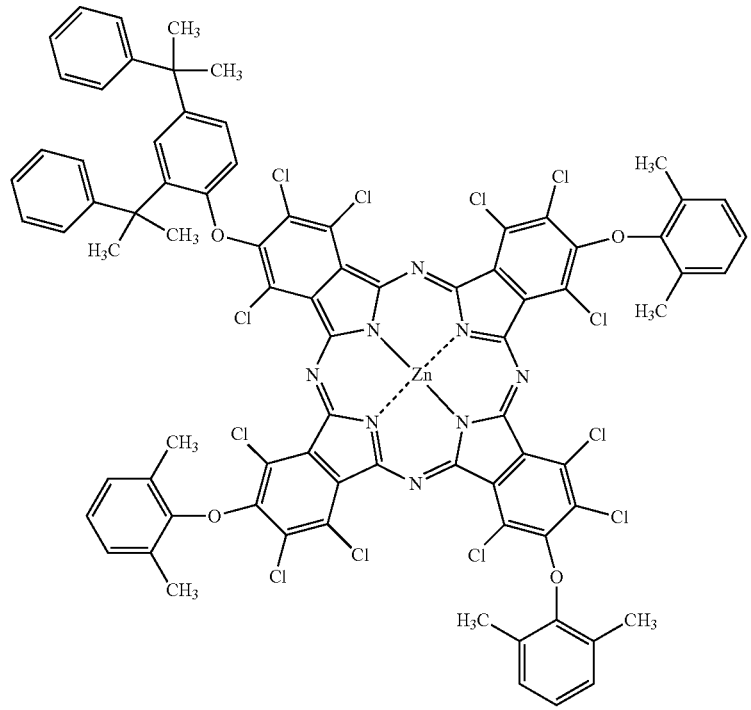

-continued

[Chemical Formula 16]

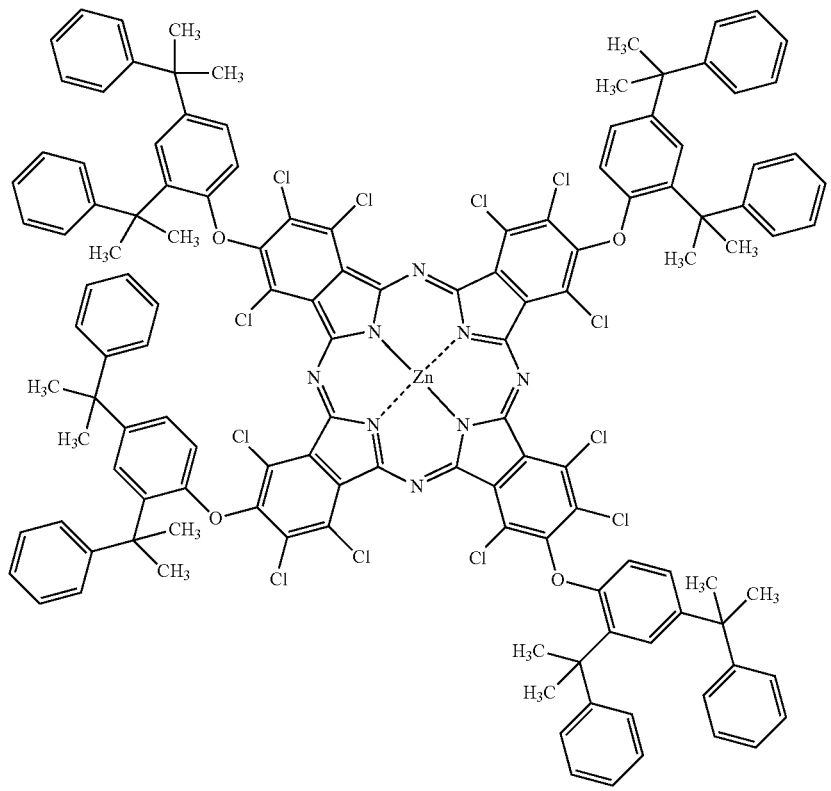

The compound may be a green dye.

The green dye may have a maximum transmittance in a wavelength of about 445 nm to about 560 nm.

Another embodiment provides a photosensitive resin composition including the compound. The photosensitive resin composition may further include an alkali soluble resin, a photopolymerizable compound, a photopolymerization initiator, and a solvent.

The photosensitive resin composition may further include a pigment.

The pigment may be a yellow pigment.

Yet another embodiment provides a color filter manufactured using the photosensitive resin composition.

Other embodiments of the present invention are included in the following detailed description.

The compound according to exemplary embodiments can have excellent green spectral characteristics, a high molar extinction coefficient, and excellent solubility for an organic solvent and thus may be used as a dye during preparation of a photosensitive resin composition for a green color filter, and a color filter including the dye may have excellent luminance, a contrast ratio, and transmittance.

DETAILED DESCRIPTION

The present invention will be described more fully hereinafter, in which exemplary embodiments of the present invention are described. This invention may, however, be embodied in many different forms and should not be construed as limited to the exemplary embodiments set forth herein. These exemplary embodiments disclosed in this specification are provided so that this disclosure will satisfy applicable legal requirements.

As used herein, when a specific definition is not otherwise provided, the term "substituted" refers to one substituted with at least one or more substituents selected from a halogen (F, Cl, Br or I), a hydroxy group, a nitro group, a thiol group, a cyano group, an amino group ($NH_2$, $NH(R^{200})$ or $N(R^{201})(R^{202})$,) wherein $R^{200}$, $R^{201}$ and $R^{202}$ are the same or different and are each independently a C1 to C10 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group and/or a substituted or unsubstituted heterocyclic group, in place of at least one hydrogen atom.

As used herein, when a specific definition is not otherwise provided, the term "alkyl group" refers to a C1 to C20 alkyl group, for example a C1 to C15 alkyl group, the term "cycloalkyl group" refers to a C3 to C20 cycloalkyl group, for example a C3 to C18 cycloalkyl group, the term "alkoxy group" refers to a C1 to C20 alkoxy group, for example a C1 to C18 alkoxy group, the term "aryl group" refers to a C6 to C20 aryl group, for example a C6 to C18 aryl group, the term "alkenyl group" refers to a C2 to C20 alkenyl group, for example a C2 to C18 alkenyl group, the term "alkynyl group" refers to a C2 to C20 alkynyl group, for example a C2 to C18 alkynyl group, the term "alkylene group" refers to a C1 to C20 alkylene group, for example a C1 to C18 alkylene group, and the term "arylene group" refers to a C6 to C20 arylene group, for example a C6 to C16 arylene group.

Also as used herein, unless other specified, the term "alicyclic organic group" refers to a C3 to C40 cycloalkyl group, a C3 to C40 cycloalkenyl group, a C3 to C40 cycloalkynyl group, a C3 to C40 cycloalkylene group, a C3 to C40 cycloalkenylene group, or a C3 to C40 cycloalkynylene group, for example a C3 to C20 cycloalkyl group, a C3 to C20 cycloalkenyl group, a C3 to C20 cycloalkynyl group, a C3 to C20 cycloalkylene group, a C3 to C20 cycloalkenylene group, or a C3 to C20 cycloalkynylene group.

Also as used herein, unless other specified, the term "heterocyclic group" refers to an alicyclic organic group as defined herein including at least one heteroatom replacing at least one cyclic ring carbon atom, a C2 to C40 heteroaryl group, or a C2 to C40 heteroarylene group, for example a C2 to C16 heteroaryl group or a C2 to C16 heteroarylene group.

As used herein, when a specific definition is not otherwise provided, the term "hetero" refers to at least one hetero atom of N, O, S and/or P, instead of at least one carbon atom of a cyclic substituent.

As used herein, when a specific definition is not otherwise provided, "(meth)acrylate" refers to "acrylate" and "methacrylate," and "(meth)acrylic acid" refers to "acrylic acid" and "methacrylic acid."

As used herein, when a definition is not otherwise provided, the term "combination" refers to mixing and/or copolymerization. In addition, "copolymerization" refers to block copolymerization and/or random copolymerization, and "copolymer" refers to a block copolymer and/or a random copolymer.

In the chemical formula of the present specification, unless a specific definition is otherwise provided, hydrogen is bonded at a position when a chemical bond is not drawn where a bond would otherwise appear.

As used herein, when a specific definition is not otherwise provided, "*" indicates a point where the same or different atom or Chemical Formula is linked.

Exemplary embodiments provide a compound represented by the following Chemical Formula 1:

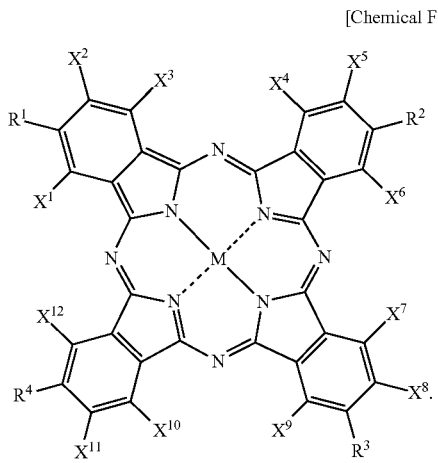

[Chemical Formula 1]

In Chemical Formula 1,
M is Zn or Cu,
$X^1$ to $X^{12}$ are the same or different and are each independently a hydrogen atom or a halogen atom,
$R^1$ to $R^4$ are the same or different and are each independently a hydrogen atom, a halogen atom, a substituted or unsubstituted C1 to C20 alkyl group, a substituted or unsubstituted C3 to C20 alkoxy group, a substituted or unsubstituted C6 to C20 aryl group, or a substituted or unsubstituted C6 to C20 aryloxy group, provided that at least one of $R^1$ to $R^4$ is represented by Chemical Formula 2,

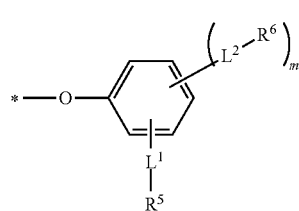

[Chemical Formula 2]

wherein, in Chemical Formula 2,
$L^1$ and $L^2$ are the same or different and are each independently a single bond or a substituted or unsubstituted C1 to C10 alkylene group,
provided that $L^1$ and $L^2$ are not simultaneously a single bond,
$R^5$ and $R^6$ are the same or different and are each independently a substituted or unsubstituted C3 to C20 cycloalkyl group or a substituted or unsubstituted C6 to C20 aryl group,
provided that when $L^1$ is a single bond, $R^5$ is a substituted or unsubstituted C3 to C20 cycloalkyl group, and
m is an integer of 0 or 1.

For example, when $L^1$ is a single bond, $R^5$ may be a substituted or unsubstituted C3 to C20 cycloalkyl group, and when $L^2$ is a single bond, $R^6$ may be a substituted or unsubstituted C3 to C20 cycloalkyl group.

The compound represented by Chemical Formula 1 according to exemplary embodiments can have excellent green spectral characteristics and a high luminance. Furthermore, the compound represented by Chemical Formula 1 necessarily includes the aryloxy group represented by Chemical Formula 2, and thus may have excellent solubility for an organic solvent, luminance, and transmittance.

In exemplary embodiments, M may be Zn.

For example, Chemical Formula 2 may be represented by Chemical Formula 3:

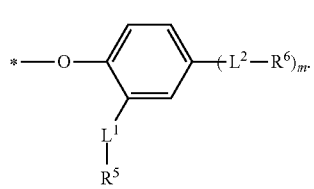

[Chemical Formula 3]

In Chemical Formula 3,
$L^1$ is a single bond or a substituted or unsubstituted C1 to C10 alkylene group,
$L^2$ is a substituted or unsubstituted C1 to C10 alkylene group,
$R^5$ is a substituted or unsubstituted C3 to C20 cycloalkyl group,
$R^6$ is a substituted or unsubstituted C6 to C20 aryl group, and
m is an integer of 0 or 1.

When $L^1$ is a single bond and $R^5$ is a substituted or unsubstituted C3 to C20 cycloalkyl group, heat resistance can be improved and thus luminance can increase.

When $L^2$ is a substituted or unsubstituted C1 to C10 alkylene group, and $R^6$ is a substituted or unsubstituted C6 to C20 aryl group, transmittance may be improved.

For example, Chemical Formula 2 may be represented by Chemical Formula 3-1 and/or Chemical Formula 3-2:

[Chemical Formula 3-1]

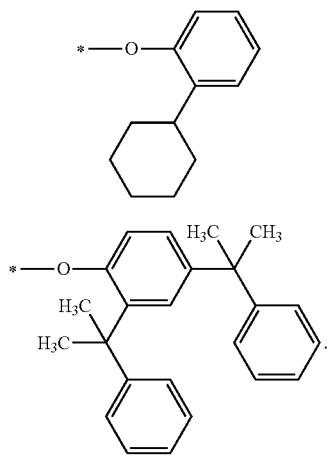

[Chemical Formula 3-2]

For example, at least two, and as another example at least three, of $R^1$ to $R^4$ may be represented by Chemical Formula 2. As another example, all of $R^1$ to $R^4$ may be represented by Chemical Formula 2.

As the number of substituents represented by Chemical Formula 2 increases, a compound according to exemplary embodiments can have improved solubility for an organic solvent.

For example, the substituted or unsubstituted C3 to C20 alkoxy group may be represented by Chemical Formula 4:

[Chemical Formula 4]

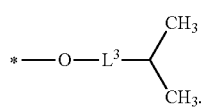

In Chemical Formula 4, $L^3$ is a single bond or a substituted or unsubstituted C1 to C17 alkylene group.

A compound according to exemplary embodiments may have improved solubility when it has the substituent represented by Chemical Formula 4.

For example, the substituted or unsubstituted C6 to C20 aryloxy group may be represented by Chemical Formula 5 and/or Chemical Formula 6:

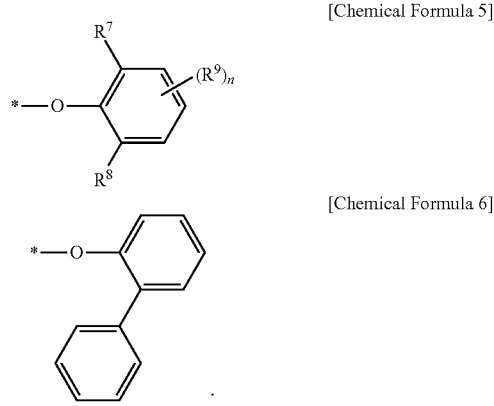

[Chemical Formula 5]

[Chemical Formula 6]

In Chemical Formula 5, $R^7$ and $R^8$ are the same or different and are each independently a substituted or unsubstituted C1 to C7 alkyl group, $R^9$ is a halogen atom, and n is an integer of 0 or 1.

The compound according to exemplary embodiments may have improved transmittance when it has the substituent represented by Chemical Formula 5 and/or Chemical Formula 6.

The compound represented by the above Chemical Formula 1 may include one or more selected from the following Chemical Formula 7 to Chemical Formula 16:

[Chemical Formula 7]

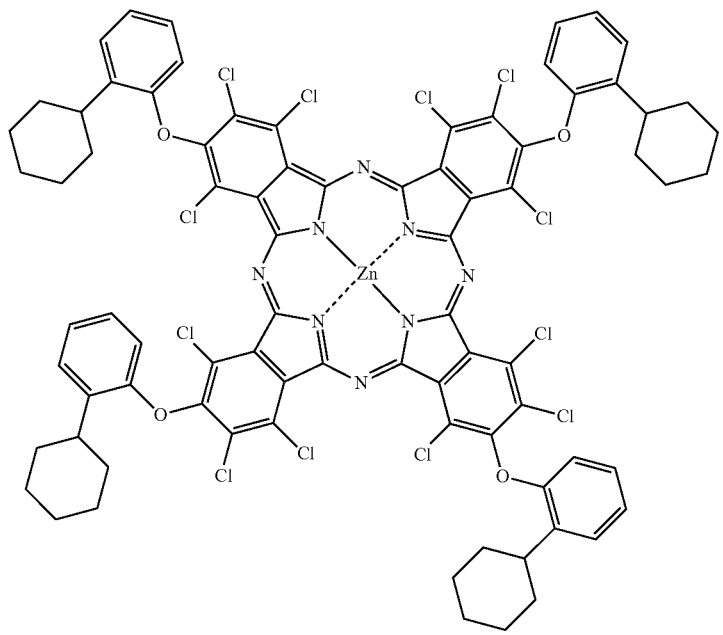

-continued
[Chemical Formula 8]
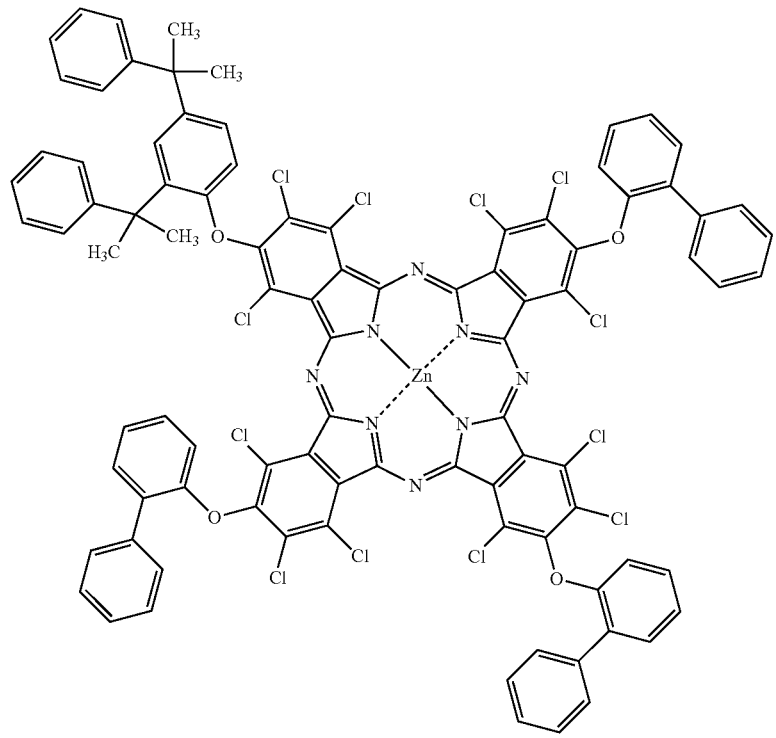
[Chemical Formula 9]
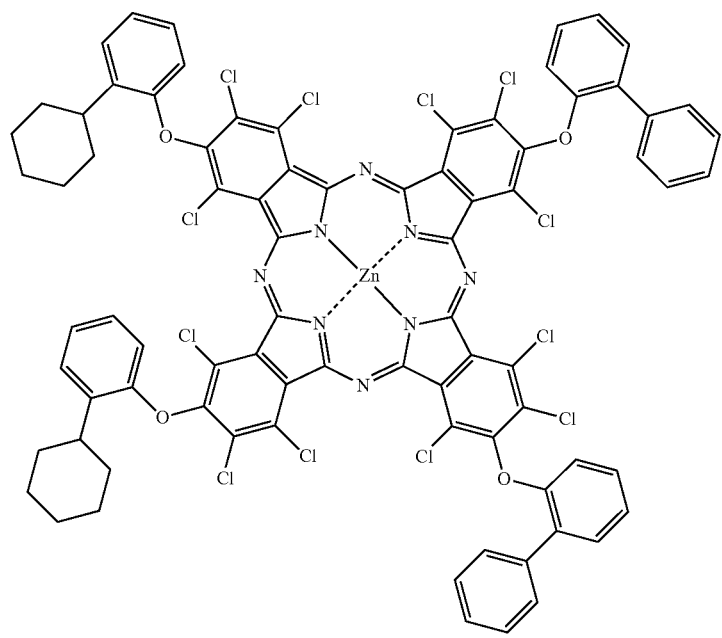

-continued
[Chemical Formula 10]
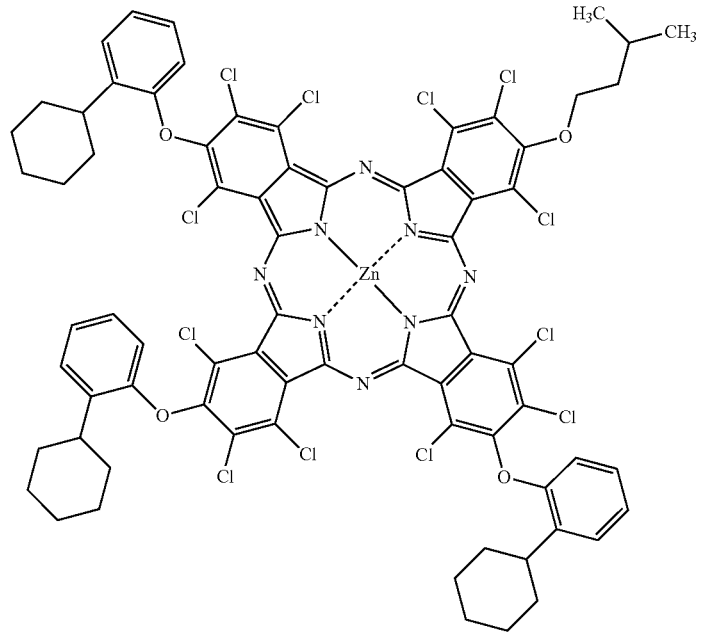
[Chemical Formula 11]
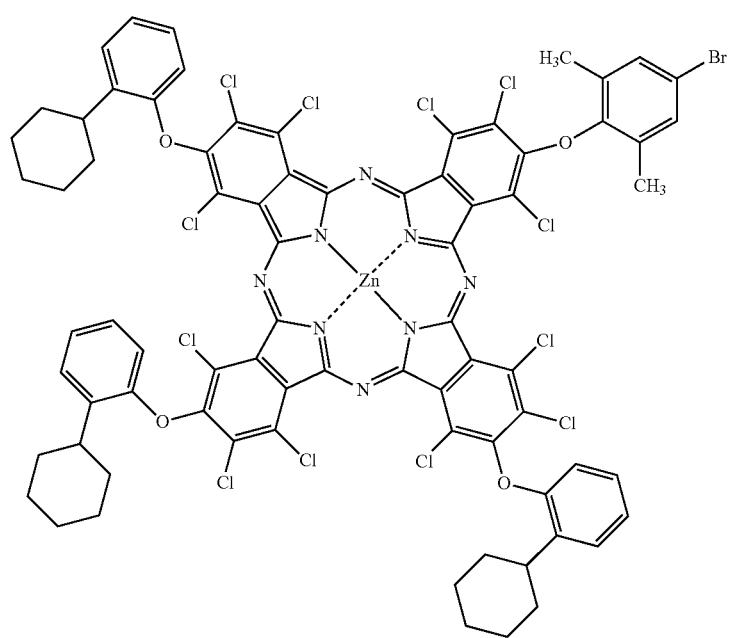

[Chemical Formula 12]
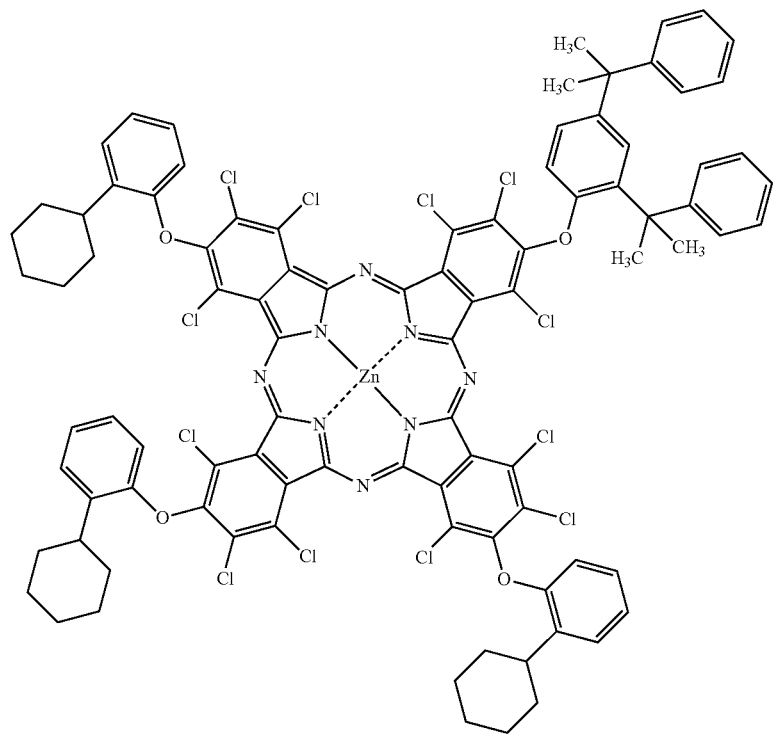
[Chemical Formula 13]
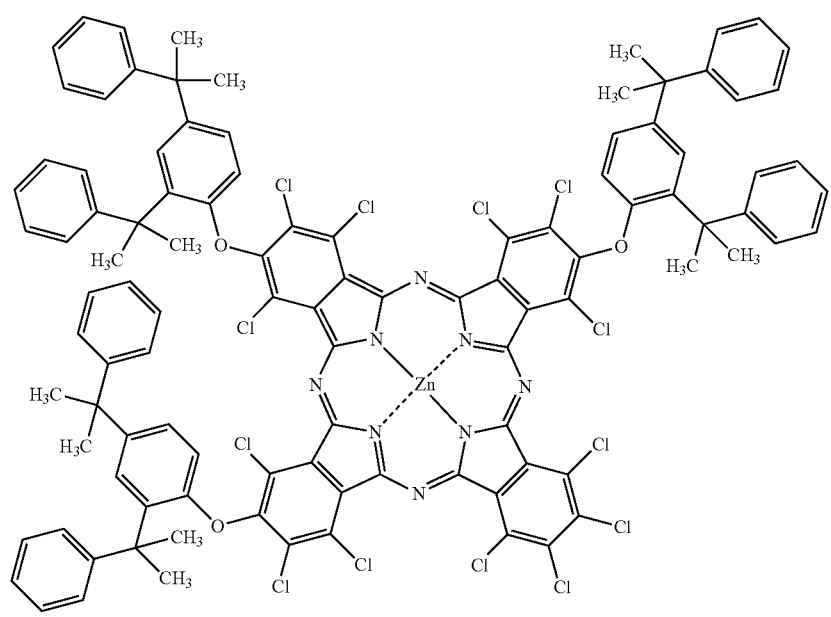

[Chemical Formula 14]
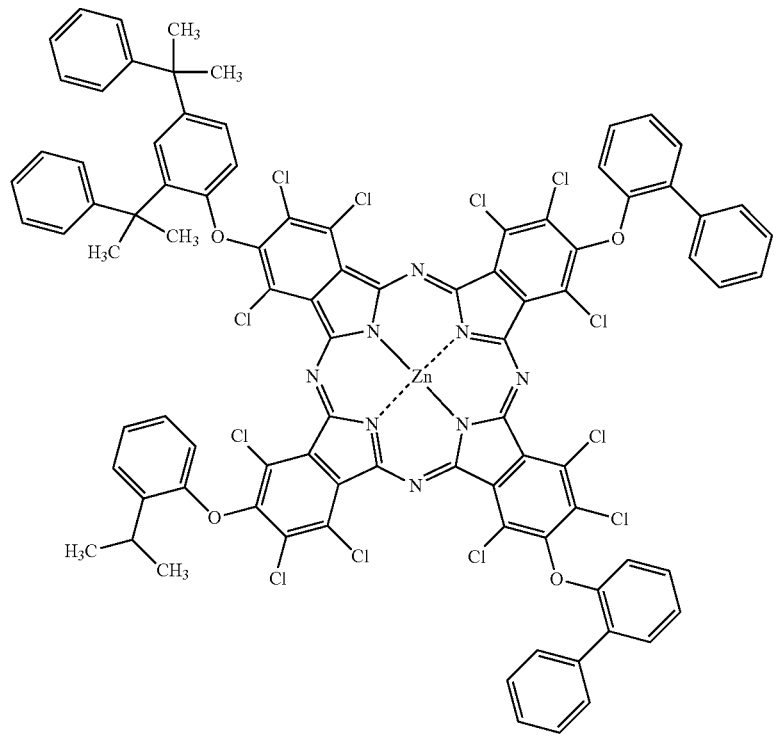
[Chemical Formula 15]
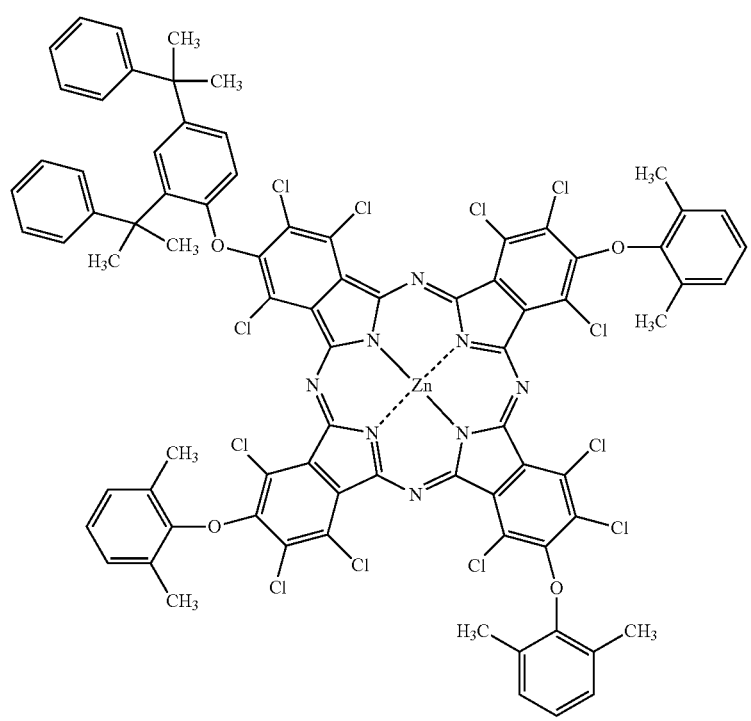

[Chemical Formula 16]

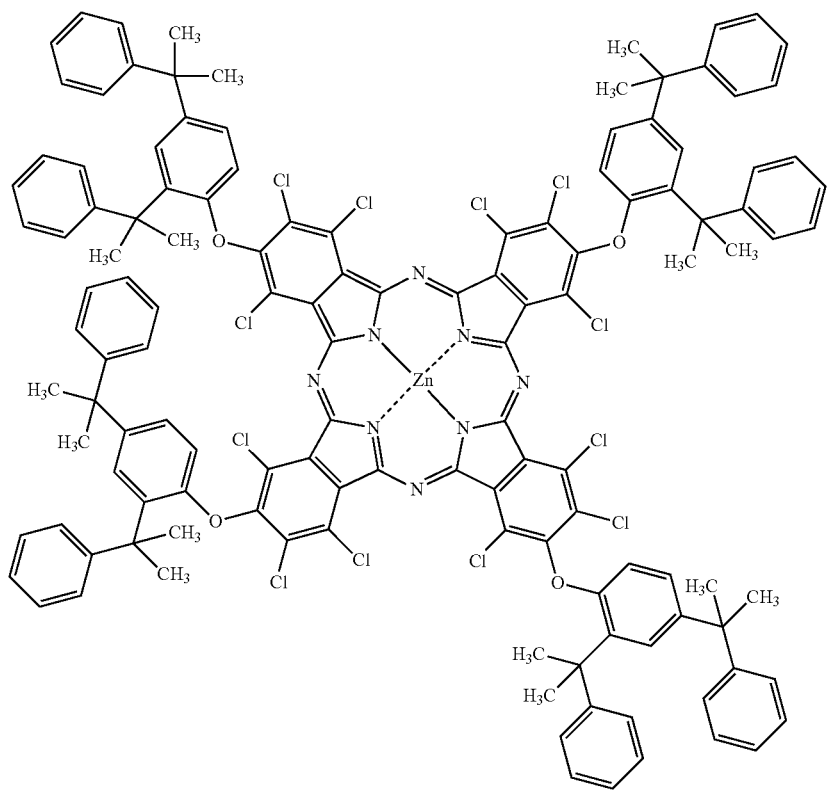

Since the compound according to exemplary embodiments may realize a clearer color even in a smaller amount, a display device having excellent color characteristics such as luminance, a contrast ratio and the like may be manufactured by using the compound as a colorant because it includes the substituent represented by Chemical Formula 2 (specifically the substituent represented by Chemical Formula 3). For example, the compound may be a colorant, for example a dye, for example a green dye, for example a dye having a maximum transmittance in a wavelength of about 445 nm to about 560 nm.

In general, a dye is the most expensive among the components used in a color filter. A large amount of the expensive dye may need to be used to accomplish a desired effect, for example, high luminance, a high contrast ratio or the like, which can increase the unit cost of production. However, when the compound according to exemplary embodiments is used as a dye in a color filter, a small amount of the compound may accomplish excellent color characteristics such as high luminance, a high contrast ratio and the like and thus can reduce the unit cost of production.

Furthermore, the compound according to exemplary embodiments may have more improved solubility for an organic solvent and transmittance when it includes a substituent represented by Chemical Formula 3-2.

According to exemplary embodiments, a photosensitive resin composition including the compound according to the above embodiment is provided.

For example, the photosensitive resin composition can include the compound according to the above embodiment, an alkali soluble resin, a photopolymerizable compound, a photopolymerization initiator, and a solvent. The photosensitive resin composition may further include a pigment.

The compound according to exemplary embodiments may play a role of a colorant, for example, a dye, and specifically, a green dye, and can realize excellent color characteristics in a photosensitive resin composition.

The photosensitive resin composition can include the compound of Chemical Formula 1 in an amount of about 1 wt % to about 10 wt %, for example about 3 wt % to about 7 wt %, based on the total weight (100 wt %) of the photosensitive resin composition. In some embodiments, the photosensitive resin composition can include the compound of Chemical Formula 1 in an amount of about 1, 2, 3, 4, 5, 6, 7, 8, 9, or 10 wt %. Further, according to some embodiments of the present invention, the amount of the compound of Chemical Formula 1 can be in a range from about any of the foregoing amounts to about any other of the foregoing amounts.

When the compound of Chemical Formula 1 is included in an amount within the above range, color reproducibility and contrast ratio may be improved.

The photosensitive resin composition may further include a pigment, for example a yellow pigment.

Examples of the yellow pigment may include without limitation C.I. pigment yellow 139, C.I. pigment yellow 138, C.I. pigment yellow 150, and the like in a color index, and these may be used alone or as a mixture of two or more.

The pigment can be included in a form of pigment dispersion liquid in the photosensitive resin composition.

The pigment dispersion liquid may include a solid pigment, a solvent, and a dispersing agent in order to disperse the pigment in the solvent uniformly.

The solid pigment may be included in an amount of about 1 wt % to about 20 wt %, for example about 8 wt % to about 20 wt %, for example about 8 wt % to about 15 wt %, for example about 10 wt % to about 20 wt %, for example about 10 wt % to about 15 wt %, based on the total weight (100 wt %) of the pigment dispersion liquid.

The dispersing agent may be a non-ionic dispersing agent, an anionic dispersing agent, a cationic dispersing agent, and the like. Specific examples of the dispersing agent may include without limitation polyalkylene glycols and esters thereof, polyoxyalkylenes, polyhydric alcohol ester alkylene oxide addition products, alcoholalkylene oxide addition products, sulfonate esters, sulfonate salts, carboxylate esters, carboxylate salts, alkylamide alkylene oxide addition products, alkyl amines, and the like, and may be used alone or as a mixture of two or more.

Commercially available examples of the dispersing agent may include without limitation DISPERBYK-101, DISPERBYK-130, DISPERBYK-140, DISPERBYK-160, DISPERBYK-161, DISPERBYK-162, DISPERBYK-163, DISPERBYK-164, DISPERBYK-165, DISPERBYK-166, DISPERBYK-170, DISPERBYK-171, DISPERBYK-182, DISPERBYK-2000, DISPERBYK-2001, and the like made by BYK Co., Ltd.; EFKA-47, EFKA-47EA, EFKA-48, EFKA-49, EFKA-100, EFKA-400, EFKA-450, and the like made by EFKA Chemicals Co.; Solsperse 5000, Solsperse 12000, Solsperse 13240, Solsperse 13940, Solsperse 17000, Solsperse 20000, Solsperse 24000GR, Solsperse 27000, Solsperse 28000, and the like made by Zeneka Co.; and/or PB711, PB821, and the like made by Ajinomoto Inc.

The dispersing agent may be included in an amount of about 1 to about 20 wt % based on the total weight (100 wt %) of the pigment dispersion liquid. When the dispersing agent is included in an amount within the above range, dispersion of a photosensitive resin composition can be improved due to an appropriate viscosity, and thus optical, physical and chemical quality may be maintained when the photosensitive resin composition is applied to products.

Examples of the solvent for forming the pigment dispersion liquid may include without limitation ethylene glycol acetate, ethylcellosolve, propylene glycol monomethyl ether acetate, ethyllactate, polyethylene glycol, cyclohexanone, propylene glycol methylether, and the like, and mixtures thereof.

The photosensitive resin composition can include the pigment dispersion liquid in an amount of about 10 wt % to about 20 wt %, for example about 12 wt % to about 18 wt %, based on the total amount (total weight, 100 wt %) of the photosensitive resin composition. In some embodiments, the photosensitive resin composition can include the pigment dispersion liquid in an amount of about 10, 11, 12, 13, 14, 15, 16, 17, 18, 19, or 20 wt %. Further, according to some embodiments of the present invention, the amount of the pigment dispersion liquid can be in a range from about any of the foregoing amounts to about any other of the foregoing amounts.

When the pigment dispersion liquid is included in an amount within the above range, a process margin may be ensured, and color reproducibility and a contrast ratio can be improved.

The alkali soluble resin may be an acrylic-based resin.

The acrylic-based resin is a copolymer of a first ethylenic unsaturated monomer and a second ethylenic unsaturated monomer that is copolymerizable therewith, and is a resin including at least one acrylic-based repeating unit.

The first ethylenic unsaturated monomer is an ethylenic unsaturated monomer including at least one carboxyl group. Examples of the monomer include without limitation (meth) acrylic acid, maleic acid, itaconic acid, fumaric acid, and the like, and combinations thereof.

The acrylic-based resin can include the first ethylenic unsaturated monomer in an amount of about 5 to about 50 wt %, for example about 10 to about 40 wt %, based on the total amount (total weight, 100 wt %) of the acrylic-based resin.

Examples of the second ethylenic unsaturated monomer may include without limitation aromatic vinyl compounds such as styrene, α-methylstyrene, vinyl toluene, vinylbenzylmethylether and the like; unsaturated carboxylate ester compounds such as methyl(meth)acrylate, ethyl(meth)acrylate, butyl(meth)acrylate, 2-hydroxyethyl(meth)acrylate, 2-hydroxy butyl(meth)acrylate, benzyl(meth)acrylate, cyclohexyl(meth)acrylate, phenyl(meth)acrylate, and the like; unsaturated carboxylic acid amino alkyl ester compounds such as 2-aminoethyl(meth)acrylate, 2-dimethylaminoethyl(meth)acrylate, and the like; carboxylic acid vinyl ester compounds such as vinyl acetate, vinyl benzoate, and the like; unsaturated carboxylic acid glycidyl ester compounds such as glycidyl(meth)acrylate, and the like; vinyl cyanide compounds such as (meth)acrylonitrile and the like; unsaturated amide compounds such as (meth)acrylamide, and the like; and the like, and may be used alone or as a mixture of two or more.

Examples of the acrylic-based resin may include without limitation an acrylic acid/benzylmethacrylate copolymer, a methacrylic acid/benzylmethacrylate copolymer, a methacrylic acid/benzylmethacrylate/styrene copolymer, a methacrylic acid/benzylmethacrylate/2-hydroxyethylmethacrylate copolymer, a methacrylic acid/benzylmethacrylate/styrene/2-hydroxyethylmethacrylate copolymer, and the like. These may be used alone or as a mixture of two or more.

The alkali soluble resin may have a weight average molecular weight of about 3,000 g/mol to about 150,000 g/mol, for example about 5,000 g/mol to about 50,000 g/mol, and as another example about 20,000 g/mol to about 30,000 g/mol. When the alkali soluble resin has a weight average molecular weight within the above range, the photosensitive resin composition can have good physical and chemical properties, appropriate viscosity, and close contacting (adhesive) properties with a substrate during manufacture of a color filter.

The alkali soluble resin may have an acid value of about 15 mgKOH/g to about 60 mgKOH/g, for example about 20 mgKOH/g to about 50 mgKOH/g. When the alkali soluble resin has an acid value within the above range, a pixel pattern may have excellent resolution.

The photosensitive resin composition can include the alkali soluble resin in an amount of about 1 wt % to about 30 wt %, for example about 1 wt % to about 20 wt %, based on the total amount (total weight, 100 wt %) of the photosensitive resin composition. In some embodiments, the photosensitive resin composition can include the alkali soluble resin in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %. Further, according to some embodiments of the present invention, the amount of the alkali soluble resin can be in a range from about any of the foregoing amounts to about any other of the foregoing amounts.

When the alkali soluble resin is included in an amount within the above range, developability may be improved and excellent surface smoothness may be improved due to improved cross-linking during the manufacture of a color filter.

The photopolymerizable compound may include a mono-functional and/or multi-functional ester of (meth)acrylic acid including at least one ethylenic unsaturated double bond.

The photopolymerizable compound has the ethylenic unsaturated double bond and thus may cause sufficient polymerization during exposure in a pattern-forming process and form a pattern having excellent heat resistance, light resistance, and chemical resistance.

Examples of the photopolymerizable compound may include without limitation ethylene glycol di(meth)acrylate, diethylene glycol di(meth)acrylate, triethylene glycol di(meth)acrylate, propylene glycol di(meth)acrylate, neopentyl glycol di(meth)acrylate, 1,4-butanediol di(meth)acrylate, 1,6-hexanediol di(meth)acrylate, bisphenol A di(meth)acrylate, pentaerythritol di(meth)acrylate, pentaerythritol tri(meth)acrylate, pentaerythritol tetra(meth)acrylate, pentaerythritol hexa(meth)acrylate, dipentaerythritol di(meth)acrylate, dipentaerythritol tri(meth)acrylate, dipentaerythritol penta(meth)acrylate, dipentaerythritol hexa(meth)acrylate, bisphenol A epoxy(meth)acrylate, ethylene glycol monomethylether (meth)acrylate, trimethylol propane tri(meth)acrylate, tris(meth)acryloyloxyethyl phosphate, novolac epoxy (meth)acrylate, and the like, and mixtures thereof.

Commercially available examples of the photopolymerizable compound are as follows. Examples of the mono-functional ester of (meth)acrylic acid may include without limitation Aronix M-101®, M-111®, and/or M-114® (Toagosei Chemistry Industry Co., Ltd.); KAYARAD TC-110S® and/or TC-120S® (Nippon Kayaku Co., Ltd.); V-158® and/or V-2311® (Osaka Organic Chemical Ind., Ltd.), and the like. Examples of a difunctional ester of (meth)acrylic acid may include without limitation Aronix M-210®, M-240®, and/or M-6200® (Toagosei Chemistry Industry Co., Ltd.), KAYARAD HDDA®, HX-220®, and/or R-604® (Nippon Kayaku Co., Ltd.), V-260®, V-312®, and/or V-335 HP® (Osaka Organic Chemical Ind., Ltd.), and the like. Examples of a tri-functional ester of (meth)acrylic acid may include without limitation Aronix M-309®, M-400®, M-405®, M-450®, M-7100®, M-8030®, and/or M-8060® (Toagosei Chemistry Industry Co., Ltd.), KAYARAD TMPTA®, DPCA-20®, DPCA-30®, DPCA-60®, and/or DPCA-120® (Nippon Kayaku Co., Ltd.), V-295®, V-300®, V-360®, V-GPT®, V-3PA®, and/or V-400® (Osaka Yuki Kayaku Kogyo Co. Ltd.), and the like. These may be used alone or as a mixture of two or more.

The photopolymerizable compound may be treated with acid anhydride to improve developability.

The photosensitive resin composition can include the photopolymerizable compound in an amount of about 1 wt % to about 15 wt %, for example about 5 wt % to about 10 wt %, based on the total amount (total weight, 100 wt %) of the photosensitive resin composition. In some embodiments, the photosensitive resin composition can include the photopolymerizable compound in an amount of about 1, 2, 3, 4, 5, 6, 7, 8, 9, 10, 11, 12, 13, 14, or 15 wt %. Further, according to some embodiments of the present invention, the amount of the photopolymerizable compound can be in a range from about any of the foregoing amounts to about any other of the foregoing amounts.

When the photopolymerizable compound is included in an amount within the above range, the photopolymerizable compound can be sufficiently cured during exposure in a pattern-forming process and can have excellent reliability, and developability for alkali developing solution may be improved.

The photopolymerization initiator is a generally-used initiator for a photosensitive resin composition. Examples of the photopolymerization can include without limitation acetophenone-based compounds, benzophenone-based compounds, thioxanthone-based compounds, benzoin-based compounds, triazine-based compounds, oxime-based compounds, and the like, and combinations thereof.

Examples of the acetophenone-based compound may include without limitation 2,2'-diethoxy acetophenone, 2,2'-dibutoxy acetophenone, 2-hydroxy-2-methylpropinophenone, p-t-butyltrichloro acetophenone, p-t-butyldichloro acetophenone, 4-chloro acetophenone, 2,2'-dichloro-4-phenoxy acetophenone, 2-methyl-1-(4-(methylthio)phenyl)-2-morpholinopropan-1-one, 2-benzyl-2-dimethylamino-1-(4-morpholinophenyl)-butan-1-one, and the like, and combinations thereof.

Examples of the benzophenone-based compound may include without limitation benzophenone, benzoyl benzoate, benzoyl methyl benzoate, 4-phenyl benzophenone, hydroxy benzophenone, acrylated benzophenone, 4,4'-bis(dimethyl amino)benzophenone, 4,4'-bis(diethylamino)benzophenone, 4,4'-dimethylaminobenzophenone, 4,4'-dichlorobenzophenone, 3,3'-dimethyl-2-methoxybenzophenone, and the like, and combinations thereof.

Examples of the thioxanthone-based compound may include without limitation thioxanthone, 2-methylthioxanthone, isopropyl thioxanthone, 2,4-diethyl thioxanthone, 2,4-diisopropyl thioxanthone, 2-chlorothioxanthone, and the like, and combinations thereof.

Examples of the benzoin-based compound may include without limitation benzoin, benzoin methyl ether, benzoin ethyl ether, benzoin isopropyl ether, benzoin isobutyl ether, benzyldimethyl ketal, and the like, and combinations thereof.

Examples of the triazine-based compound may include without limitation 2,4,6-trichloro-s-triazine, 2-phenyl 4,6-bis(trichloromethyl)-s-triazine, 2-(3',4'-dimethoxystyryl)-4,6-bis(trichloromethyl)-s-triazine, 2-(4'-methoxynaphthyl)-4,6-bis(trichloromethyl)-s-triazine, 2-(p-methoxyphenyl)-4,6-bis(trichloromethyl)-s-triazine, 2-(p-tolyl)-4,6-bis(trichloro methyl)-s-triazine, 2-biphenyl 4,6-bis(trichloro methyl)-s-triazine, bis(trichloromethyl)-6-styryl-s-triazine, 2-(naphtho1-yl)-4,6-bis(trichloromethyl)-s-triazine, 2-(4-methoxynaphtho1-yl)-4,6-bis(trichloromethyl)-s-triazine, 2-4-bis(trichloromethyl)-6-piperonyl-s-triazine, 2-4-bis(trichloromethyl)-6-(4-methoxystyryl)-s-triazine, and the like, and combinations thereof.

Examples of the oxime-based compound may include without limitation O-acyloxime-based compounds, 2-(o-benzoyloxime)-1-[4-(phenylthio)phenyl]-1,2-octandione, 1-(o-acetyloxime)-1-[9-ethyl-6-(2-methylbenzoyl)-9H-carbazol-3-yl]ethanone, O-ethoxycarbonyl-α-oxyamino-1-phenylpropan-1-one, and the like, and combinations thereof. Examples of the O-acyloxime-based compound may include without limitation 1,2-octandione, 2-dimethylamino-2-(4-methylbenzyl)-1-(4-morpholin-4-yl-phenyl)-butan-1-one, 1-(4-phenylsulfanyl phenyl)-butane-1,2-dione 2-oxime-O-benzoate, 1-(4-phenylsulfanyl phenyl)-octane-1,2-dione2-oxime-O-benzoate, 1-(4-phenylsulfanyl phenyl)-octan-1-one oxime-O-acetate and 1-(4-phenylsulfanyl phenyl)-butan-1-oneoxime-O-acetate, and the like, and combinations thereof.

The photopolymerization initiator may further include one or more of a carbazole-based compound, a diketone-based compound, a sulfonium borate-based compound, a diazo-based compound, an imidazole-based compound, a biimidazole-based compound, and the like instead of or in addition to the above compounds.

The photopolymerization initiator may be used with a photosensitizer capable of causing a chemical reaction by absorbing light and becoming excited and then transferring its energy.

Examples of the photosensitizer may include without limitation tetraethylene glycol bis-3-mercapto propionate, pentaerythritol tetrakis-3-mercapto propionate, dipentaerythritol tetrakis-3-mercapto propionate, and the like, and combinations thereof.

The photosensitive resin composition can include the photopolymerization initiator in an amount of about 0.01 wt % to about 10 wt %, for example about 0.1 wt % to about 5 wt %, based on the total amount (total weight 100 wt %) of the photosensitive resin composition. In some embodiments, the photosensitive resin composition can include the photopolymerization initiator in an amount of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 wt %. Further, according to some embodiments of the present invention, the amount of the photopolymerization initiator can be in a range from about any of the foregoing amounts to about any other of the foregoing amounts.

When the photopolymerization initiator is included in an amount within the above range, excellent reliability may be secured due to sufficiently curing during exposure in a pattern-forming process, a pattern may have excellent resolution and close-contacting properties as well as excellent heat resistance, light resistance, and chemical resistance, and transmittance may be prevented from deterioration due to a non-reacted initiator.

The solvent is a material having compatibility with the compound or the mixture, the alkali soluble resin, the photopolymerizable compound, and the photopolymerization initiator but not reacting therewith.

Examples of the solvent may include without limitation alcohols such as methanol, ethanol, and the like; ethers such as dichloroethyl ether, n-butyl ether, diisoamyl ether, methylphenyl ether, tetrahydrofuran, and the like; glycol ethers such as ethylene glycol monomethylether, ethylene glycol monoethylether, and the like; cellosolve acetates such as methyl cellosolve acetate, ethyl cellosolve acetate, diethyl cellosolve acetate, and the like; carbitols such as methylethyl carbitol, diethyl carbitol, diethylene glycol monomethylether, diethylene glycol monoethylether, diethylene glycol dimethylether, diethylene glycol methylethylether, diethylene glycol diethylether, and the like; propylene glycol alkylether acetates such as propylene glycol methylether acetate, propylene glycol propylether acetate, and the like; aromatic hydrocarbons such as toluene, xylene and the like; ketones such as methylethylketone, cyclohexanone, 4-hydroxy-4-methyl-2-pentanone, methyl-n-propylketone, methyl-n-butylketone, methyl-n-amylketone, 2-heptanone, and the like; saturated aliphatic monocarboxylic acid alkyl esters such as ethyl acetate, n-butyl acetate, isobutyl acetate, and the like; lactate esters such as methyl lactate, ethyl lactate, and the like; oxy acetic acid alkyl esters such as oxy methyl acetate, oxy ethyl acetate, butyl oxyacetate, and the like; alkoxy acetic acid alkyl esters such as methoxy methyl acetate, methoxy ethyl acetate, methoxy butyl acetate, ethoxy methyl acetate, ethoxy ethyl acetate, and the like; 3-oxy propionic acid alkyl esters such as 3-oxy methyl propionate, 3-oxy ethyl propionate, and the like; 3-alkoxy propionic acid alkyl esters such as 3-methoxy methyl propionate, 3-methoxy ethyl propionate, 3-ethoxy ethyl propionate, 3-ethoxy methyl propionate, and the like; 2-oxy propionic acid alkyl esters such as 2-oxy methyl propionate, 2-oxy ethyl propionate, 2-oxy propyl propionate, and the like; 2-alkoxy propionic acid alkyl esters such as 2-methoxy methyl propionate, 2-methoxy ethyl propionate, 2-ethoxy ethyl propionate, 2-ethoxy methyl propionate, and the like; 2-oxy-2-methyl propionic acid esters such 2-oxy-2-methyl methyl propionate, 2-oxy-2-methyl ethyl propionate, and the like, monooxy monocarboxylic acid alkyl esters of 2-alkoxy-2-methyl alkyl propionates such as 2-methoxy-2-methyl methyl propionate, 2-ethoxy-2-methyl ethyl propionate, and the like; esters such as 2-hydroxy ethyl propionate, 2-hydroxy-2-methyl ethyl propionate, hydroxy ethyl acetate, 2-hydroxy-3-methyl methyl butanoate, and the like; ketonate esters such as ethyl pyruvate, and the like; and the like, and mixtures thereof. Additionally, high boiling point solvent such as but not limited to N-methylformamide, N,N-dimethylformamide, N-methylformanilide, N-methylacetamide, N,N-dimethylacetamide, N-methylpyrrolidone, dimethylsulfoxide, benzylethylether, dihexylether, acetylacetone, isophorone, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate, phenyl cellosolve acetate, and the like, and mixtures thereof may be also used.

Considering miscibility and reactivity, glycol ethers such as ethylene glycol monoethylether, and the like; ethylene glycol alkylether acetates such as ethyl cellosolve acetate, and the like; esters such as 2-hydroxy ethyl propionate, and the like; carbitols such as diethylene glycol monomethylether, and the like; propylene glycol alkylether acetates such as propylene glycol monomethylether acetate, propylene glycol propylether acetate, and the like; and ketones such as cyclohexanone and the like may be used.

The photosensitive resin composition can include the solvent in a balance amount, for example about 30 wt % to about 80 wt % based on the total amount (total weight, 100 wt %) of the photosensitive resin composition. In some embodiments, the photosensitive resin composition can include the solvent in an amount of about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt %. Further, according to some embodiments of the present invention, the amount of the solvent can be in a range from about any of the foregoing amounts to about any other of the foregoing amounts.

When the solvent is included in an amount within the above range, the photosensitive resin composition may have an appropriate viscosity, which can improve coating characteristics of a color filter.

The photosensitive resin composition according to another embodiment may further include an epoxy compound in order to improve a close contacting property with a substrate.

Examples of the epoxy compound can include without limitation phenol novolac epoxy compounds, tetramethyl biphenyl epoxy compounds, bisphenol A epoxy compounds, alicyclic epoxy compounds, and the like, and combinations thereof.

The epoxy compound may be included in an amount of about 0.01 parts by weight to about 20 parts by weight, for example about 0.1 parts by weight to about 10 parts by weight, based on about 100 parts by weight of the photosensitive resin composition. When the epoxy compound is included in an amount within the above range, close contacting properties, storage capability, and the like may be improved.

The photosensitive resin composition may further include a silane coupling agent having a reactive substituent such as a carboxyl group, a methacryloyl group, an isocyanate group, an epoxy group, and the like in order to improve adherence to a substrate.

Examples of the silane coupling agent can include without limitation trimethoxysilyl benzoic acid, γ-methacryl oxypropyl trimethoxysilane, vinyl triacetoxysilane, vinyl trimethoxysilane, γ-isocyanate propyl triethoxysilane, γ-glycidoxy propyl trimethoxysilane, β-(3,4-epoxycyclohexyl) ethyltrimethoxysilane, and the like. These may be used alone or in a mixture of two or more.

The silane coupling agent may be included in an amount of about 0.01 parts by weight to about 10 parts by weight based on about 100 parts by weight of the photosensitive resin composition. When the silane coupling agent is included in an amount within the above range, close contacting properties, storage properties, and the like can be improved.

The photosensitive resin composition may further include a surfactant in order to improve coating properties and inhibit generation of spots.

Examples of the surfactant may include without limitation a fluorine-based surfactant. Examples of commercially available fluorine-based surfactants can include without limitation BM-1000® and/or BM-1100® (BM Chemie Inc.); MEGAFACE F 142D®, F 172®, F 173®, and/or F 183® (Dainippon Ink Kagaku Kogyo Co., Ltd.); FULORAD FC-135®, FULORAD FC-170C®, FULORAD FC-430®, and/or FULORAD FC-431® (Sumitomo 3M Co., Ltd.); SURFLON S-112®, SURFLON S-113®, SURFLON S-131®, SURFLON S-141®, and/or SURFLON S-145® (ASAHI Glass Co., Ltd.); SH-28PA®, SH-190®, SH-193®, SZ-6032®, and/or SF-8428® (Toray Silicone Co., Ltd.), and the like, and mixtures thereof.

The surfactant may be included in an amount of about 0.001 to about 5 parts by weight based on about 100 parts by weight of the photosensitive resin composition. When the surfactant is included in an amount within the above range, coating uniformity may be ensured, stains may not be generated, and wetting properties for a glass substrate can be improved.

The photosensitive resin composition may further one or more other additives such as but not limited to an antioxidant, a stabilizer, and the like in a predetermined amount. The amount of the additive(s) may be controlled to provide desired properties with minimal or no reduction of the composition properties such as described herein. The amount of the additive(s) can be readily determined by the skilled artisan.

According to another embodiment of the present invention, a color filter manufactured using the photosensitive resin composition is provided.

An exemplary pattern-forming process for the color filter is as follows.

The process can include coating the positive photosensitive resin composition on a support substrate using a method such as spin coating, slit coating, inkjet printing, and the like; drying the coated positive photosensitive resin composition to form a positive photosensitive resin composition film; exposing the positive photosensitive resin composition film to light; developing the exposed positive photosensitive resin composition film in an alkali aqueous solution to obtain a photosensitive resin film; and heat-treating the photosensitive resin film. Conditions for the patterning process are well known in a related art and will not be illustrated in detail in the specification.

Hereinafter, the present invention is illustrated in more detail with reference to examples and comparative examples. The following examples and comparative examples are provided for the purpose of illustration only and the present invention is not limited thereto.

SYNTHESIS OF COMPOUND

Synthesis Example 1

Synthesis of 3,5,6-Trichloro-4-(2-cyclohexylphenoxy)-phthalonitrile 3,4,5,6-tetrachlorophthalonitrile (5 g), 2-cyclohexylphenol (3.3143 g), $K_2CO_3$ (3.898 g), and N,N-dimethylformamide (50 ml) are put in a 100 ml flask and stirred while heated at 70° C. When a reaction is complete, an extraction is performed by using EA (ethyl acetate). After the extraction, a liquid purified through a column chromatography with EA/hexane is concentrated to obtain a solid, and the solid is vacuum-dried to obtain a compound according to Synthesis Example 1.

Synthesis Example 2

Synthesis of 3,5,6-Trichloro-4-(Biphenyl-2-yloxy)-phthalonitrile 3,4,5,6-tetrachlorophthalonitrile (5 g), 2-phenylphenol (3.201 g), $K_2CO_3$ (3.898 g), and acetone (50 ml) are put in a 100 ml flask and then stirred while heated at 50° C. When a reaction is complete, an extraction is performed with EA (ethyl acetate). After the extraction, a liquid column-purified through column chromatography with EA/hexane is concentrated to obtain a solid, and the solid is vacuum-dried, obtaining a compound according to Synthesis Example 2.

Synthesis Example 3

Synthesis of 3,5,6-Trichloro-4-(2,4-(bis-a,a-dimethylbenzyl)phenoxy)-phthalonitrile 3,4,5,6-tetrachlorophthalonitrile (5 g), 2,4-(bis-a,a-dimethylbenzyl)phenol (6.2139 g), $K_2CO_3$ (3.898 g), and N,N-dimethylformamide (50 ml) are put in a 100 ml flask and then stirred while heated at 70° C. When a reaction is complete, an extraction is performed with EA (ethyl acetate). After the extraction, a liquid column-purified through column chromatography with EA/hexane is concentrated to obtain a solid, and the solid is vacuum-dried, obtaining a compound according to Synthesis Example 3.

Synthesis Example 4

Synthesis of 3,5,6-Trichloro-4-(3-methyl-butoxy)-phthalonitrile 3,4,5,6-tetrachlorophthalonitrile (5 g), isoamyl alcohol (5.9 g), 1,8-diazabicycloundec-7-ene (3.898 g), and tetrahydrofuran (50 ml) are in a 100 ml flask and then stirred while heated at 50° C. When a reaction is complete, an extraction is performed with EA (ethyl acetate). After the extraction, a liquid column-purified through column chromatography with EA/hexane is concentrated to obtain a solid, and the solid is vacuum-dried, obtaining a compound according to Synthesis Example 4.

Synthesis Example 5

Synthesis of 3,5,6-Trichloro-4-(2,6-dimethyl-4-bromophenoxy)-phthalonitrile 3,4,5,6-tetrachlorophthalonitrile (5 g), 2,6-dimethyl-4-bromophenol (3.78 g), $K_2CO_3$ (3.898 g), and N,N-dimethylformamide (50 ml) are put in a 100 ml flask and then stirred while heated at 60° C. When a reaction is complete, an extraction is performed with EA (ethyl acetate). After the extraction, a liquid column-purified through column chromatography with EA/hexane is concentrated to obtain a solid, and the solid is vacuum-dried, obtaining a compound according to Synthesis Example 5.

Synthesis Example 6

Synthesis of 3,5,6-Trichloro-4-(2-isopropylphenoxy)-phthalonitrile 3,4,5,6-tetrachlorophthalonitrile (5 g), 2-isopropylphenol (2.5608 g), $K_2CO_3$ (3.898 g), and N,N-dimethylformamide (50 ml) are put in a 100 ml flask and then stirred while heated at 50° C. When a reaction is complete, an extraction is performed with EA (ethyl acetate). After the extraction, a liquid column-purified through column chromatography with EA/hexane is concentrated to obtain a solid, and the solid is vacuum-dried, obtaining a compound according to Synthesis Example 6.

Synthesis Example 7

Synthesis of 3,5,6-Trichloro-4-(2,6-dimethylphenoxy)-phthalonitrile 3,4,5,6-tetrachlorophthalonitrile (5 g), 2,6-dimethylphenol (2.2972 g), $K_2CO_3$ (3.898 g), and N,N-dimethylformamide (50 ml) are put in a 100 ml flask and then stirred while heated at 60° C. When a reaction is complete, an extraction is performed with EA (ethyl acetate). After the extraction, a liquid column-purified through column chromatography with EA/hexane is concentrated to obtain a solid, and the solid is vacuum-dried, obtaining a compound according to Synthesis Example 7.

Synthesis Example 8

Synthesis of Compound Represented by Chemical Formula 7

The compound according to Synthesis Example 1 (2 g), benzonitrile (8 g), and 1-pentenol (15 ml) are put in a 100 ml flask and heated at 90° C., and then, when the solids dissolved, zinc acetate (0.2261 g) is added thereto, and the mixture is continuously stirred, while heated at 140° C. When a reaction is complete, a precipitate therein is filtered with MeOH and vacuum-dried. The dried solid is purified through column chromatography. Then, dichloromethane in a small amount is added to the solid to dissolve therein, and methanol is added thereto for crystallization. Herein, a solid obtained therefrom is filtered and vacuum-dried, obtaining a compound represented by Chemical Formula 7.

[Chemical Formula 7]

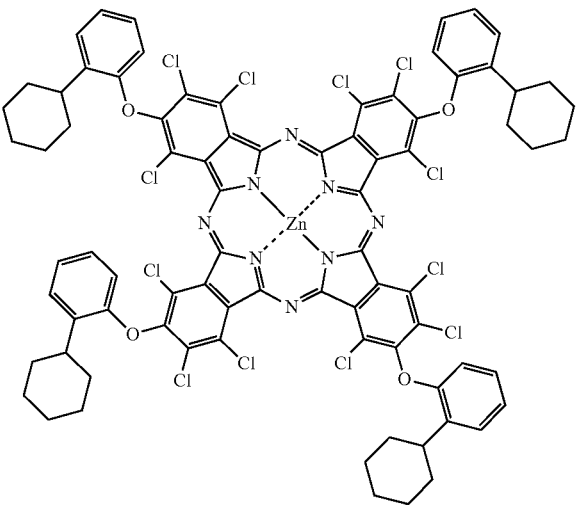

MALDI-TOF MS, m/z Calcd. For 1687.02 m/z

Synthesis Example 9

Synthesis of Compound Represented by Chemical Formula 8

The compound (1.392 g) according to Synthesis Example 2, the compound (0.65 g) according to Synthesis Example 3, benzonitrile (8 g), and 1-pentenol (15 ml) are put in a 100 ml flask and heated at 90° C., and then when the solids therein dissolved, zinc acetate (0.2130 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the solid to dissolve therein, and methanol is added thereto for crystallization. Herein, a solid therefrom is filtered and vacuum-dried, obtaining a compound represented by Chemical Formula 8.

[Chemical Formula 8]

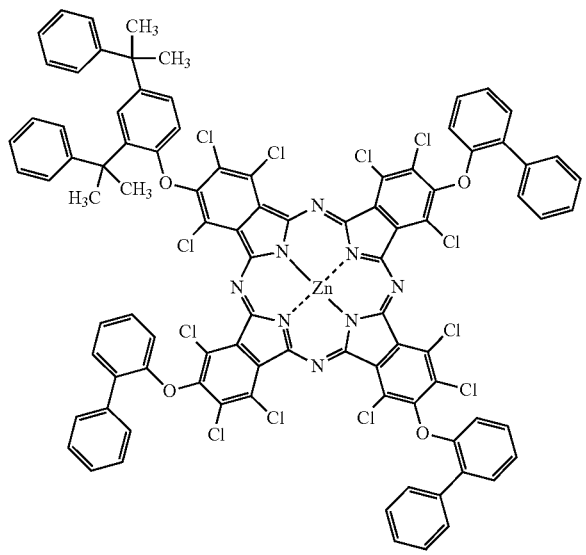

MALDI-TOF MS, m/z Calcd. For 1821.96 m/z

Synthesis Example 10

Synthesis of Compound Represented by Chemical Formula 9

The compound (1 g) according to Synthesis Example 1, the compound (0.985 g) according to Synthesis Example 2, benzonitrile (8 g), and 1-pentenol (15 ml) are put in a 100 ml flask and heated at 90° C., and when the solids dissolved, zinc acetate (0.2261 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, the obtained solid is filtered and vacuum-dried, obtaining a compound represented by Chemical Formula 9.

[Chemical Formula 9]

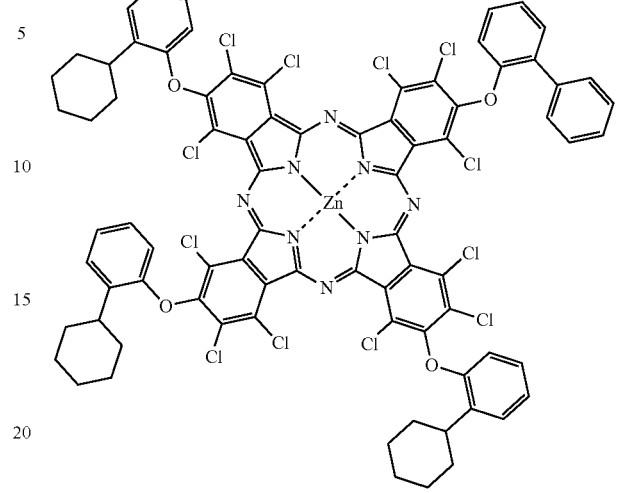

MALDI-TOF MS, m/z Calcd. For 1674.93 m/z

Synthesis Example 11

Synthesis of Compound Represented by Chemical Formula 10

The compound (1.533 g) according to Synthesis Example 1, the compound (0.4 g) according to Synthesis Example 4, benzonitrile (8 g), and 1-pentenol (15 ml) are put in a 100 ml flask and heated at 90° C., and when the solids dissolved, zinc acetate (0.2311 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, the obtained solid is filter and vacuum-dried, obtaining a compound represented by Chemical Formula 10.

[Chemical Formula 10]

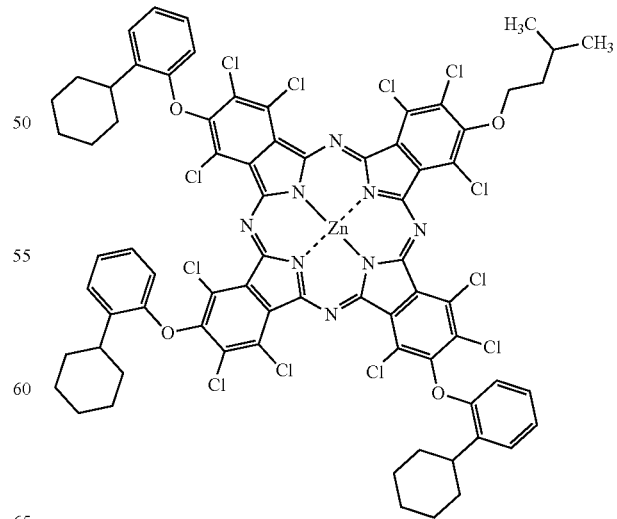

MALDI-TOF MS, m/z Calcd. For 1587.99 m/z

Synthesis Example 12
Synthesis of Compound Represented by Chemical Formula 11

The compound (1.5 g) according to Synthesis Example 1, the compound (0.5305 g) according to Synthesis Example 5, benzonitrile (8 g), and 1-pentenol (15 ml) are put in a 100 ml flask and heated at 90° C., and when the solids dissolved, zinc acetate (0.2261 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, the obtained solid is filtered and vacuum-dried, obtaining a compound represented by Chemical Formula 11.

[Chemical Formula 11]

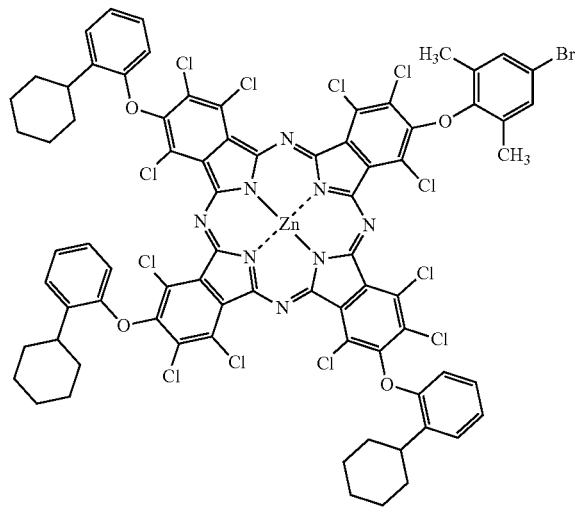

MALDI-TOF MS, m/z Calcd. For 1709.88 m/z

Synthesis Example 13
Synthesis of Compound Represented by Chemical Formula 12

The compound (1.4 g) according to Synthesis Example 1, the compound (0.644 g) according to Synthesis Example 3, benzonitrile (8 g), and 1-pentenol (15 ml) are put in a 100 ml flask and heated at 90° C., and when the solids dissolved, zinc acetate (0.211 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, the obtained solid is filtered and vacuum-dried, obtaining a compound represented by Chemical Formula 12.

[Chemical Formula 12]

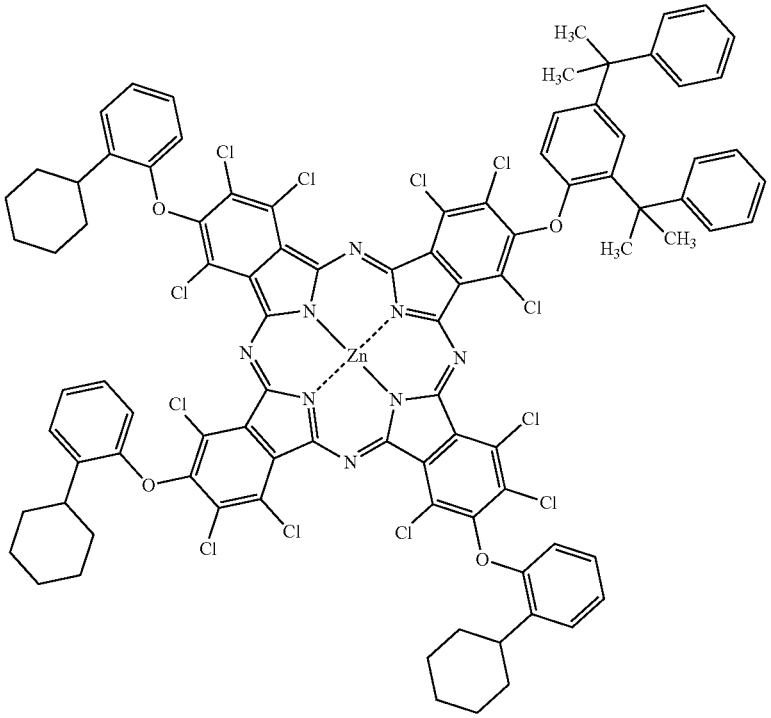

MALDI-TOF MS, m/z Calcd. For 1840.10 m/z

Synthesis Example 14

Synthesis of Compound Represented by Chemical Formula 13

The compound (1.7 g) according to Synthesis Example 3, 3,4,5,6-tetrachlorophthalonitrile (0.2691 g), benzonitrile (8 g), and 1-pentenol (15 ml) are put in a 100 ml flask and heated at 90° C., and when the solids dissolved, zinc acetate (0.1857 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, the obtained solid is filtered and vacuum-dried, obtaining a compound represented by Chemical Formula 13.

[Chemical Formula 13]

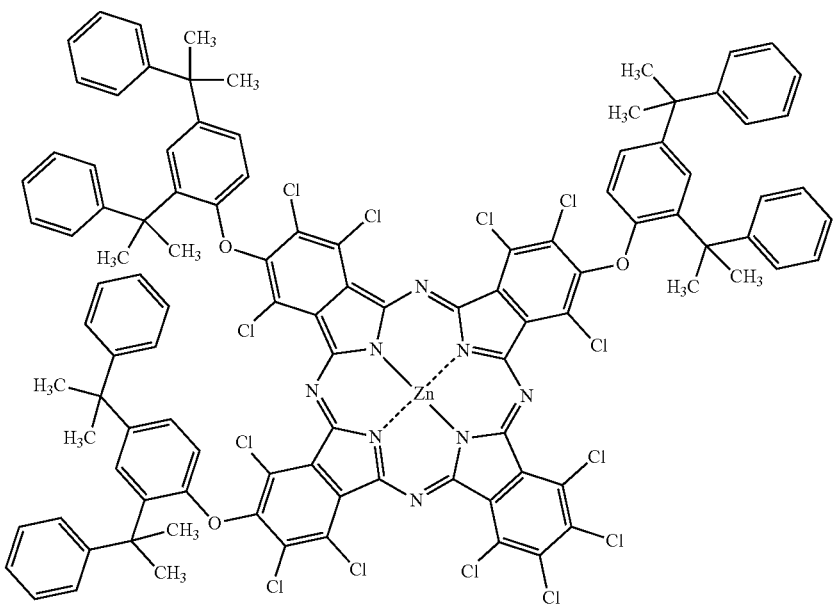

MALDI-TOF MS, m/z Calcd. For 2009.11 m/z

Synthesis Example 15

Synthesis of Compound Represented by Chemical Formula 14

The compound (0.9279 g) according to Synthesis Example 2, the compound (0.65 g) according to Synthesis Example 3, the compound (0.4245 g) according to Synthesis Example 6, benzonitrile (8 g), and 1-pentenol (15 ml) are put in a 100 ml flask and heated at 90° C., and when a solid therein is dissolved, zinc acetate (0.2130 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, a solid obtained therefrom is filtered and vacuum-dried, obtaining a compound represented by Chemical Formula 14.

[Chemical Formula 14]

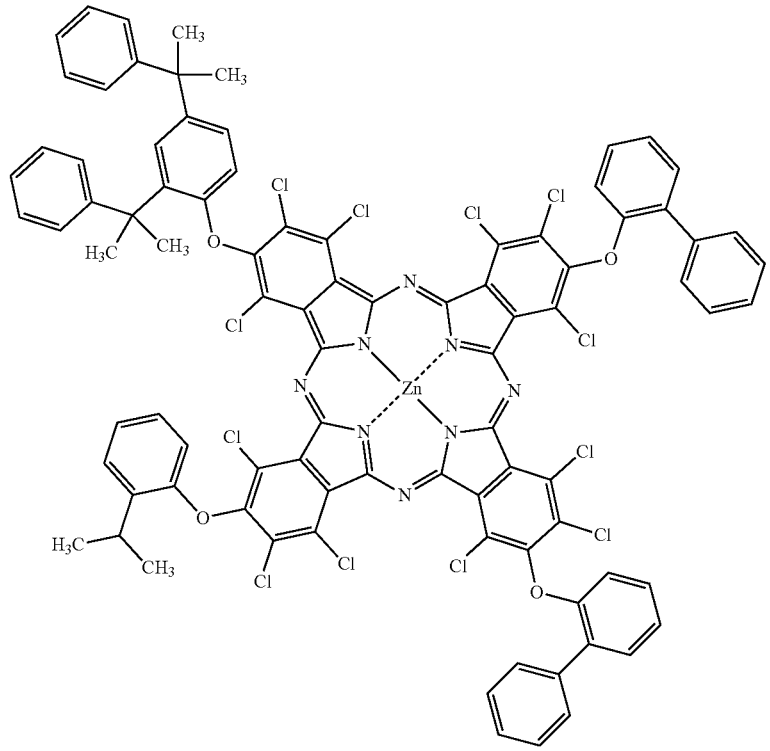

MALDI-TOF MS, m/z Calcd. For 1787.97 m/z

Synthesis Example 16

Synthesis of Compound Represented by Chemical Formula 15

The compound (0.7 g) according to Synthesis Example 3, the compound (1.3187 g) according to Synthesis Example 7, benzonitrile (8 g), and 1-pentenol (15 ml) are put in a 100 ml flask and heated at 90° C., and when a solid therein is dissolved, zinc acetate (0.211 g) is added thereto, and the mixture is stirred, while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, the obtained solid is filtered and vacuum-dried, obtaining a compound represented by Chemical Formula 15.

[Chemical Formula 15]

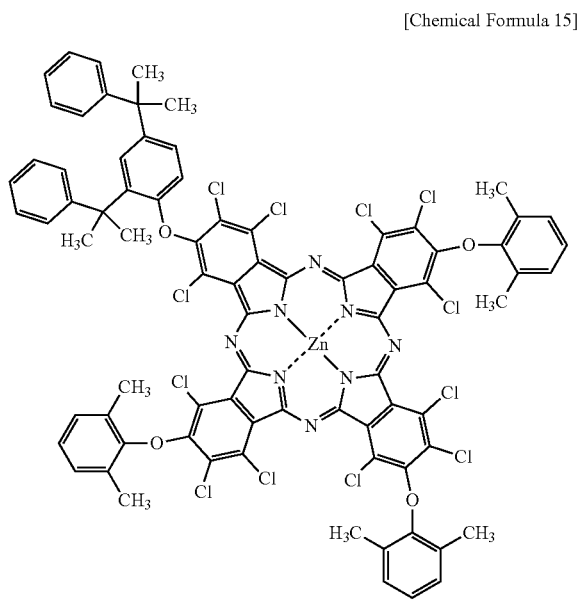

MALDI-TOF MS, m/z Calcd. For 1678.96 m/z

Synthesis Example 17

Synthesis of Compound Represented by Chemical Formula 16

The compound (2 g) according to Synthesis Example 3, benzonitrile (8 g), and 1-pentenol (15 ml) are put in a 100 ml flask and heated at 90° C., and when a solid therein is dissolved, zinc acetate (0.1638 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, a solid obtained therefrom is filtered and vacuum-dried, obtaining a compound represented by Chemical Formula 16.

[Chemical Formula 16]

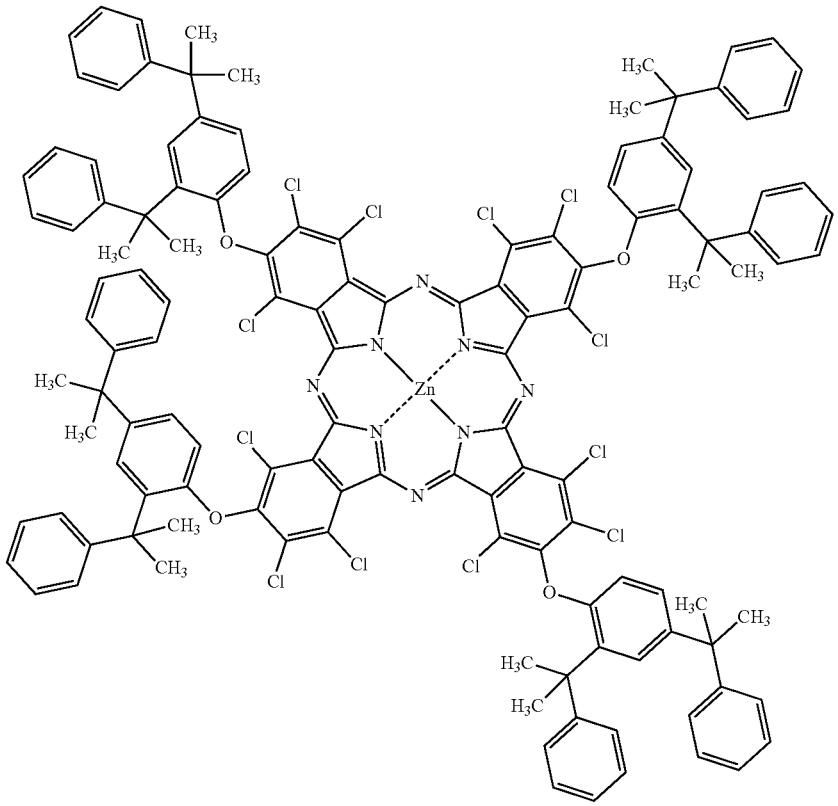

MALDI-TOF MS, m/z Calcd. For 2303.34 m/z

Comparative Synthesis Example 1

Synthesis of Compound Represented by Chemical Formula 17

3,5,6-trichloro-4-(phenoxy)phthalonitrile (2 g), benzonitrile (8 g), and 1-pentenol (15 mL) are put in a 100 mL flask and heated at 90° C., and when a solid therein is dissolved, zinc acetate (0.2835 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, a solid obtained therefrom is filtered and vacuum-dried, obtaining a compound represented by Chemical Formula 17.

[Chemical Formula 17]

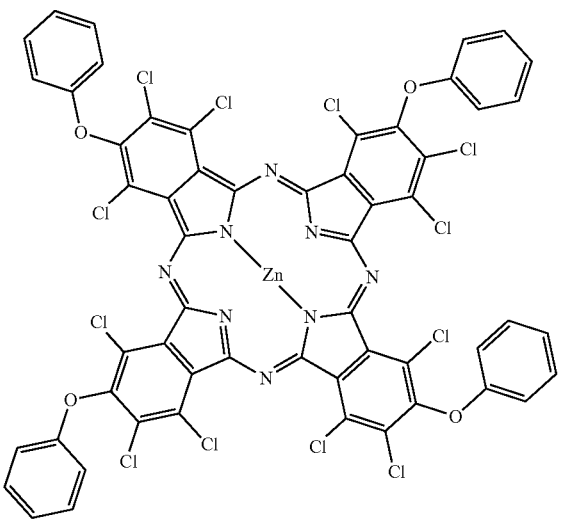

MALDI-TOF MS, m/z Calcd. For 1355.71 m/z

Comparative Synthesis Example 2

Synthesis of Compound Represented by Chemical Formula 18

3,5,6-trichloro-4-(pentyloxy)phthalonitrile (2 g), benzonitrile (8 g), and 1-pentenol (15 mL) are put in a 100 mL flask and heated at 90° C., and when a solid therein is dissolved, zinc acetate (0.2889 g) is added thereto, and the mixture is stirred while continuously heated at 140° C. When a reaction is complete, a precipitate therein is filtered with MeOH and vacuum-dried. The dried solid is purified through column chromatography. Then, dichloromethane in a small amount is added to the obtained solid to dissolve therein, and methanol is added thereto for crystallization. Herein, the obtained solid is filtered and vacuum-dried, obtaining a compound represented by Chemical Formula 18.

[Chemical Formula 18]

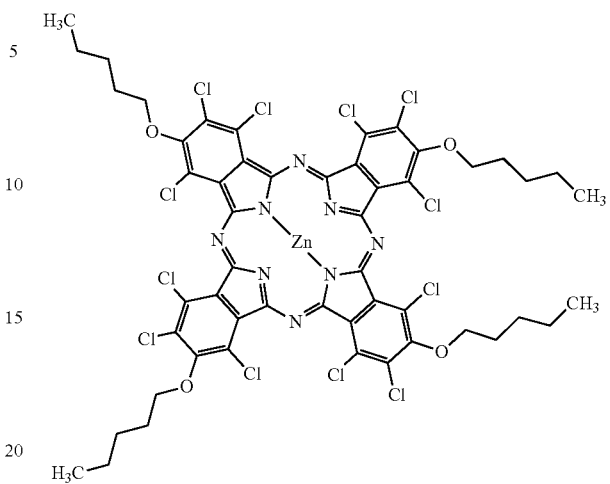

MALDI-TOF MS, m/z Calcd. For 1333.90 m/z

Evaluation 1: Solubility Measurement

A dilution solvent (PGMEA) is respectively added to 0.5 g of the compounds according to Synthesis Examples 8 to 17 and Comparative Synthesis Examples 1 and 2, and each solution is stirred with a mixrotar (MIXROTAR VMR-5, Iuchi Seieido Co., Ltd.) at 25° C. and 100 rpm for one hour. Solubility results of the compounds are provided in Table 1.

Reference for Solubility Evaluation

Greater than or equal to 10 wt % of a compound (a solute) is dissolved based on the total amount of a dilution solvent: ○

Greater than or equal to 5 wt % but less than 10 wt % of a compound (a solute) is dissolved based on the total amount of a dilution solvent: Δ

Less than 5 wt % of a compound (a solute) is dissolved based on the total amount of a dilution solvent: X

TABLE 1

| | (unit: wt %) |
|---|---|
| | Solubility |
| Synthesis Example 8 | ○ |
| Synthesis Example 9 | ○ |
| Synthesis Example 10 | ○ |
| Synthesis Example 11 | ○ |
| Synthesis Example 12 | ○ |
| Synthesis Example 13 | ○ |
| Synthesis Example 14 | ○ |
| Synthesis Example 15 | ○ |
| Synthesis Example 16 | ○ |
| Synthesis Example 17 | ○ |
| Comparative Synthesis Example 1 | x |
| Comparative Synthesis Example 2 | Δ |

Referring to Table 1, each compound of Synthesis Examples 8 to 17 according to one embodiment shows excellent solubility in an organic solvent and thus may show excellent color characteristics when used for a resin composition and the like compared with each compound of Comparative Synthesis Examples 1 and 2.

Synthesis of Photosensitive Resin Composition

Example 1

A photosensitive resin composition according to Example 1 is manufactured by mixing the following components in a composition provided in Table 2.

Specifically, a photopolymerization initiator is dissolved in a solvent, the solution is stirred at room temperature for 2 hours, an alkali soluble resin and a photopolymerizable compound are added thereto, and the mixture is stirred at room temperature for 2 hours. Then, the compound (represented by Chemical Formula 7) according to Synthesis Example 8 and a pigment (in a pigment dispersion liquid state) as a colorant are added to the reactant, and the mixture is stirred at room temperature for one hour. Then, the product is three times filtered to remove impurities, preparing a photosensitive resin composition.

TABLE 2

(unit: wt %)

| Composition materials | | | Amounts |
|---|---|---|---|
| Colorant | Dye | Compound of Synthesis Example 6 | 5.0 |
| | Pigment dispersion liquid | Pigment Y138 pigment dispersion liquid | 15.0 |
| Alkali soluble resin | | (A)/(B) = 15/85(w/w), molecular weight (Mw) = 22,000 g/mol (A): methacrylic acid (B): benzylmethacrylate | 3.5 |
| Photopolymerizable compound | | Dipentaerythritolhexaacrylate (DPHA) | 8.0 |
| Photopolymerization initiator | | 1,2-octandione | 1.0 |
| | | 2-dimethylamino-2-(4-methyl-benzyl)-1-(4-morpholin-4-yl-phenyl)-butan-1-one | 0.5 |
| | Solvent | cyclohexanone | 37.0 |
| | | PGMEA (Propylene Glycol Monomethyl Ether Acetate) | 30.0 |
| | | Total | 100.00 |

Example 2

A photosensitive resin composition is prepared according to the same method as Example 1 except for using the compound (represented by Chemical Formula 8) according to Synthesis Example 9 instead of the compound (represented by Chemical Formula 7) according to Synthesis Example 8.

Example 3

A photosensitive resin composition is prepared according to the same method as Example 1 except for using the compound (represented by Chemical Formula 9) according to Synthesis Example 10 instead of the compound (represented by Chemical Formula 7) according to Synthesis Example 8.

Example 4

A photosensitive resin composition is prepared according to the same method as Example 1 except for using the compound (represented by Chemical Formula 10) according to Synthesis Example 11 instead of the compound (represented by Chemical Formula 7) according to Synthesis Example 8.

Example 5

A photosensitive resin composition is prepared according to the same method as Example 1 except for using the compound (represented by Chemical Formula 11) according to Synthesis Example 12 instead of the compound (represented by Chemical Formula 7) according to Synthesis Example 8.

Example 6

A photosensitive resin composition is prepared according to the same method as Example 1 except for using the compound (represented by Chemical Formula 12) according to Synthesis Example 13 instead of the compound (represented by Chemical Formula 7) according to Synthesis Example 8.

Example 7

A photosensitive resin composition is prepared according to the same method as Example 1 except for using the compound (represented by Chemical Formula 13) according to Synthesis Example 14 instead of the compound (represented by Chemical Formula 7) according to Synthesis Example 8.

Example 8

A photosensitive resin composition is prepared according to the same method as Example 1 except for using the compound (represented by Chemical Formula 14) according to Synthesis Example 15 instead of the compound (represented by Chemical Formula 7) according to Synthesis Example 8.

Example 9

A photosensitive resin composition is prepared according to the same method as Example 1 except for using the compound (represented by Chemical Formula 15) according to Synthesis Example 16 instead of the compound (represented by Chemical Formula 7) according to Synthesis Example 8.

Example 10

A photosensitive resin composition is prepared according to the same method as Example 1 except for using the compound (represented by Chemical Formula 16) according to Synthesis Example 17 instead of the compound (represented by Chemical Formula 7) according to Synthesis Example 8.

Comparative Example 1

A photosensitive resin composition is prepared according to the same method as Example 1 except for using the compound (represented by Chemical Formula 17) according to Comparative Synthesis Example 1 instead of the compound (represented by Chemical Formula 7) according to Synthesis Example 8.

Comparative Example 2

A photosensitive resin composition was prepared according to the same method as Example 1 except for using the compound (represented by Chemical Formula 18) according to Comparative Synthesis Example 2 instead of the compound (represented by Chemical Formula 7) according to Synthesis Example 8.

Comparative Example 3

A photosensitive resin composition is prepared according to the same method as Example 1 except for using the composition provided in Table 3 instead of the composition provided in Table 2.

TABLE 3

(unit: wt %)

| | Composition materials | | Amounts |
|---|---|---|---|
| Colorant | Pigment dispersion liquid | Pigment G58 pigment dispersion liquid | 20.0 |
| | | Pigment Y138 pigment dispersion liquid | 15.0 |
| Alkali soluble resin | | (A)/(B) = 15/85 (w/w), molecular weight (Mw) = 22,000 g/mol (A): methacrylic acid (B): benzylmethacrylate | 2.5 |
| Photopolymerizable compound | | Dipentaerythritolhexaacrylate (DPHA) | 5.0 |
| Photopolymerization initiator | | 1,2-octandione | 1.0 |
| | | 2-dimethylamino-2-(4-methyl-benzyl)-1-(4-morpholin-4-yl-phenyl)-butan-1-one | 0.5 |
| Solvent | | cyclohexanone | 40.0 |
| | | PGMEA (Propylene Glycol Monomethyl Ether Acetate) | 16.0 |
| Total | | | 100.00 |

Evaluation 2: Measurement of Color Coordinate, Luminance and Contrast Ratio

The photosensitive resin compositions according to Examples 1 to 10 and Comparative Examples 1 to 3 are respectively coated to be 1 μm to 3 μm thick on a 1 mm-thick degreased glass substrate and dried on a 90° C. hot plate for 2 minutes, obtaining each film. Subsequently, the film is exposed to light by using a high pressure mercury lamp with a main wavelength of 365 nm. The film is dried in a 200° C. forced convection drying furnace for 5 minutes. As for a pixel layer, a color coordinate (x, y), luminance (Y) and a contrast ratio are measured by using a spectrophotometer (MCPD3000, Otsuka Electronics Inc.), and the results are provided in Table 4.

TABLE 4

| | Color coordinate (x, y) | Luminance (Y) | Contrast ratio |
|---|---|---|---|
| Example 1 | 0.281, .0.580 | 62.6 | 15,600 |
| Example 2 | 0.278, 0.574 | 62.9 | 15,500 |
| Example 3 | 0.279, 0.575 | 62.8 | 15,100 |
| Example 4 | 0.280, 0.581 | 62.9 | 15,300 |
| Example 5 | 0.280, 0.580 | 62.4 | 15,400 |
| Example 6 | 0.275, 0.575 | 62.1 | 15,700 |
| Example 7 | 0.277, 0.573 | 62.7 | 15,200 |
| Example 8 | 0.276, 0.576 | 62.2 | 15,300 |
| Example 9 | 0.280, 0.578 | 63.0 | 15,000 |
| Example 10 | 0.279, 0.581 | 62.3 | 15,100 |
| Comparative Example 1 | 0.277, 0.578 | 60.5 | 14,900 |
| Comparative Example 2 | 0.276, 0.580 | 59.1 | 14,100 |
| Comparative Example 3 | 0.271, 0.579 | 59.0 | 13,300 |

Referring to Table 4, the photosensitive resin compositions of Examples 1 to 10 including a compound according to one embodiment of the present invention as a dye show excellent color characteristics compared with the photosensitive resin compositions of Comparative Examples 1 to 3 not including the compound.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A compound represented by the following Chemical Formula 1:

[Chemical Formula 1]

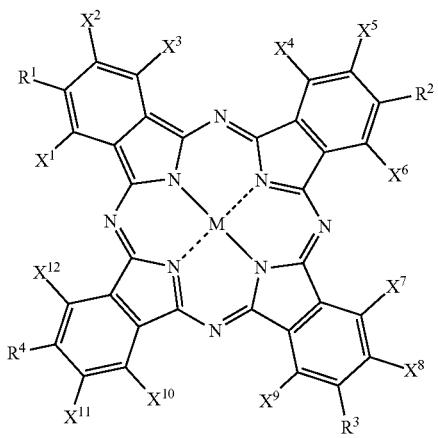

wherein, in Chemical Formula 1,

M is Zn or Cu, $X^1$ to $X^{12}$ are the same or different and are each independently a hydrogen atom or a halogen atom, $R^1$ to $R^4$ are the same or different and are each independently a hydrogen atom, a halogen atom, a substituted or unsubstituted C1 to C20 alkyl group, a substituted or unsubstituted C3 to C20 alkoxy group, a substituted or unsubstituted C6 to C20 aryl group, or a substituted or unsubstituted C6 to C20 aryloxy group, provided at least one of $R^1$ to $R^4$ is represented by Chemical Formula 3,

[Chemical Formula 3]

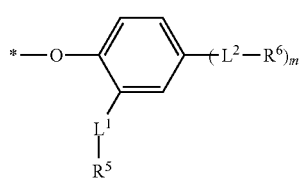

wherein, in Chemical Formula 3,
$L^1$ is a single bond or a substituted or unsubstituted C1 to C10 alkylene group,
$L^2$ is a substituted or unsubstituted C1 to C10 alkylene group,
$R^5$ is a substituted or unsubstituted C3 to C20 cycloalkyl group,
$R^6$ is a substituted or unsubstituted C6 to C20 aryl group, and
m is an integer of 0 or 1.

2. The compound of claim 1, wherein Chemical Formula 3 is represented by Chemical Formula 3-1:

[Chemical Formula 3-1]

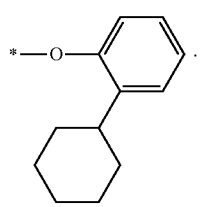

3. The compound of claim 1, wherein at least two of $R^1$ to $R^4$ are represented by Chemical Formula 3.

4. The compound of claim 1, wherein at least three of $R^1$ to $R^4$ are represented by Chemical Formula 3.

5. The compound of claim 1, wherein all of $R^1$ to $R^4$ are represented by Chemical Formula 3.

6. The compound of claim 1, wherein the substituted or unsubstituted C3 to C20 alkoxy group is represented by Chemical Formula 4:

[Chemical Formula 4]

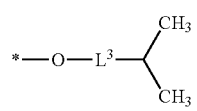

wherein, in Chemical Formula 4,
$L^3$ is a single bond or a substituted or unsubstituted C1 to C17 alkylene group.

7. The compound of claim 1, wherein the substituted or unsubstituted C6 to C20 aryloxy group is represented by Chemical Formula 5 or Chemical Formula 6:

[Chemical Formula 5]

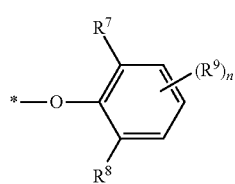

[Chemical Formula 6]

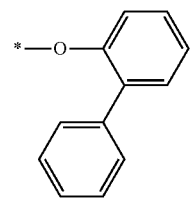

wherein, in Chemical Formula 5,
$R^7$ and $R^8$ are the same or different and are each independently a substituted or unsubstituted C1 to C7 alkyl group,
$R^9$ is a halogen atom, and
n is an integer of 0 or 1.

8. The compound of claim 1, wherein the compound represented by Chemical Formula 1 is selected from one or more of Chemical Formula 7, Chemical Formula 9, Chemical Formula 10, Chemical Formula 11, and Chemical Formula 12:

[Chemical Formula 7]

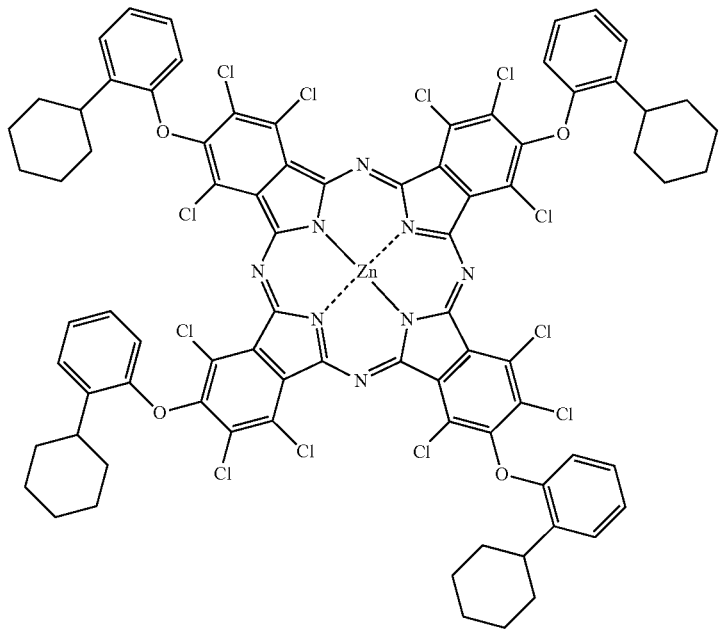

[Chemical Formula 9]
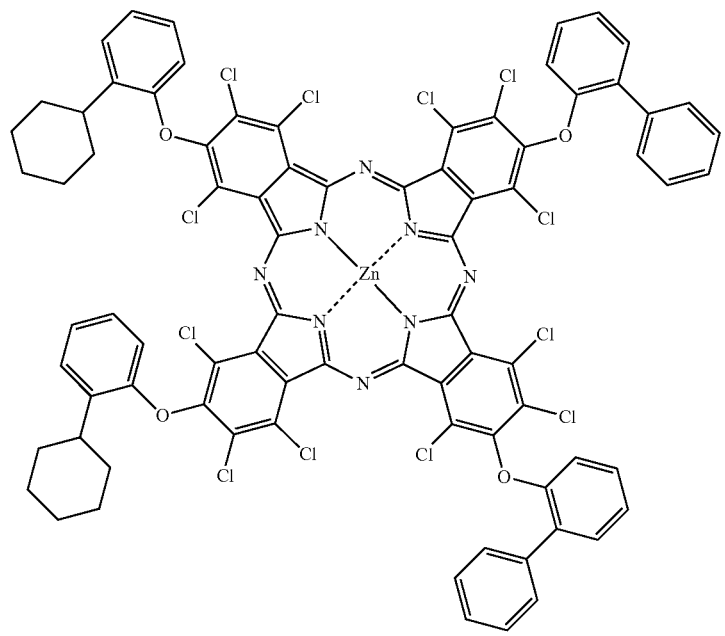
[Chemical Formula 10]
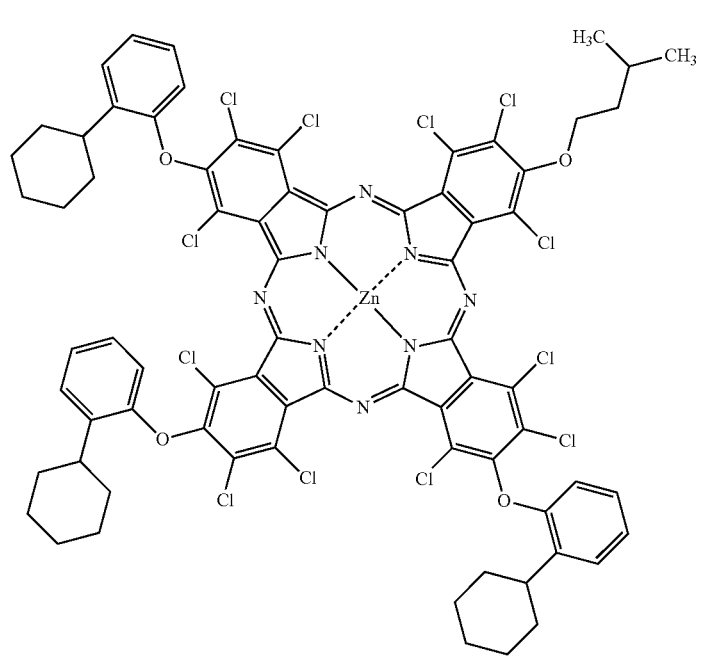

[Chemical Formula 11]
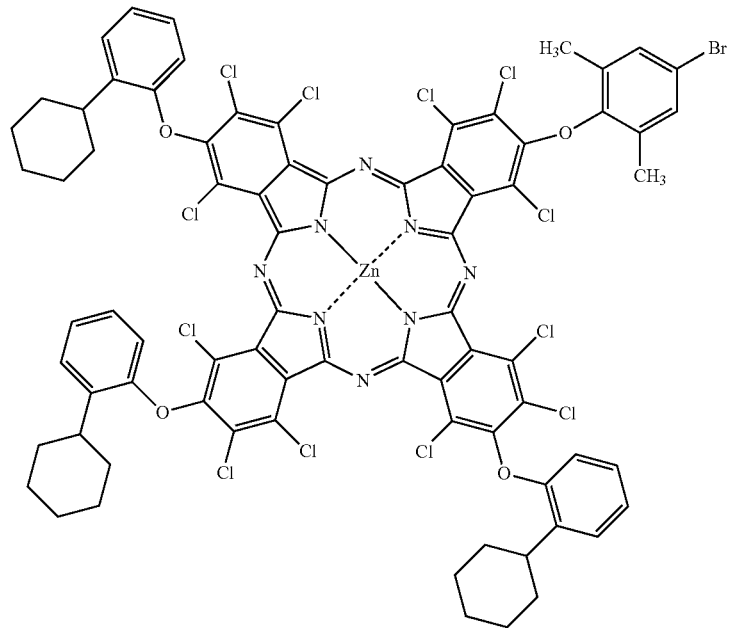
[Chemical Formula 12]
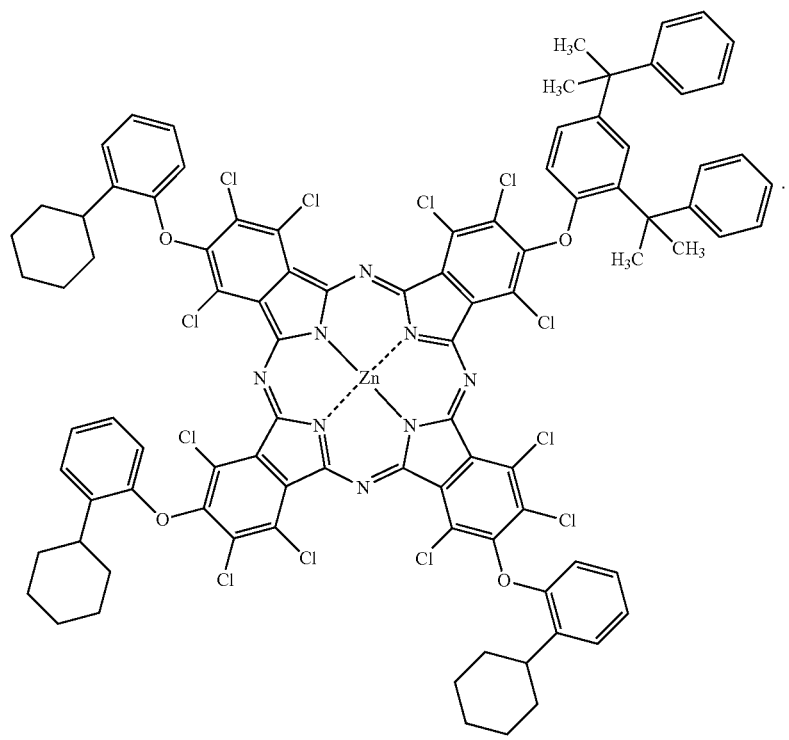

9. The compound of claim 1, wherein the compound is a green dye.

10. The compound of claim 9, wherein the green dye has a maximum transmittance in a wavelength of about 445 nm to about 560 nm.

11. A photosensitive resin composition comprising a compound represented by the following Chemical Formula 1:

[Chemical Formula 1]

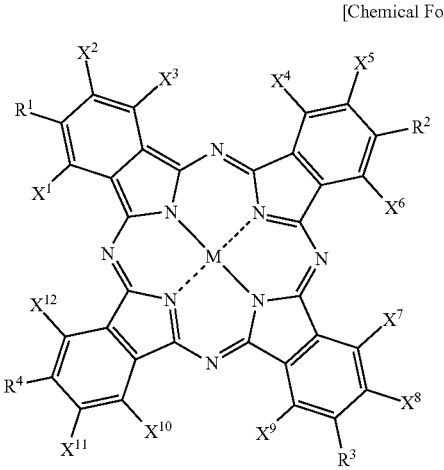

wherein, in Chemical Formula 1,
M is Zn or Cu,
$X^1$ to $X^{12}$ are the same or different and are each independently a hydrogen atom or a halogen atom,
$R^1$ to $R^4$ are the same or different and are each independently a hydrogen atom, a halogen atom, a substituted or unsubstituted C1 to C20 alkyl group, a substituted or unsubstituted C3 to C20 alkoxy group, a substituted or unsubstituted C6 to C20 aryl group, or a substituted or unsubstituted C6 to C20 aryloxy group, provided at least one of $R^1$ to $R^4$ is represented by Chemical Formula 2,

[Chemical Formula 2]

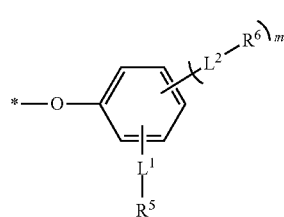

wherein, in Chemical Formula 2,
$L^1$ and $L^2$ are the same or different and are each independently a single bond or a substituted or unsubstituted C1 to C10 alkylene group,
provided that $L^1$ and $L^2$ are not simultaneously a single bond,
$R^5$ and $R^6$ are the same or different and are each independently a substituted or unsubstituted C3 to C20 cycloalkyl group or a substituted or unsubstituted C6 to C20 aryl group,
provided that when $L^1$ is a single bond, $R^5$ is a substituted or unsubstituted C3 to C20 cycloalkyl group, and
m is an integer of 0 or 1.

12. The photosensitive resin composition of claim 11, wherein the photosensitive resin composition further comprises an alkali soluble resin, a photopolymerizable compound, a photopolymerization initiator, and a solvent.

13. The photosensitive resin composition of claim 12, wherein the photosensitive resin composition further comprises a pigment.

14. A color filter manufactured using the photosensitive resin composition of claim 11.

15. The photosensitive resin composition of claim 11, wherein Chemical Formula 2 is represented by Chemical Formula 3:

[Chemical Formula 3]

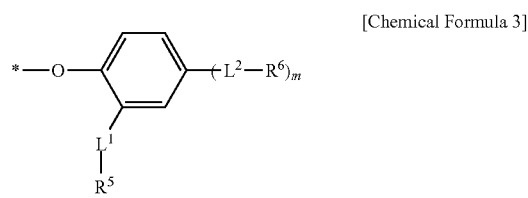

wherein, in Chemical Formula 3,
$L^1$ is a single bond or a substituted or unsubstituted C1 to C10 alkylene group,
$L^2$ is a substituted or unsubstituted C1 to C10 alkylene group,
$R^5$ is a substituted or unsubstituted C3 to C20 cycloalkyl group,
$R^6$ is a substituted or unsubstituted C6 to C20 aryl group, and
m is an integer of 0 or 1.

16. The photosensitive resin composition of claim 11, wherein Chemical Formula 2 is represented by Chemical Formula 3-1:

[Chemical Formula 3-1]

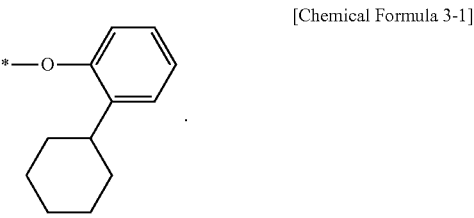 [SMILES: *Oc1ccccc1C1CCCCC1]

17. The photosensitive resin composition of claim 11, wherein Chemical Formula 2 is represented by Chemical Formula 3-2:

[Chemical Formula 3-2]

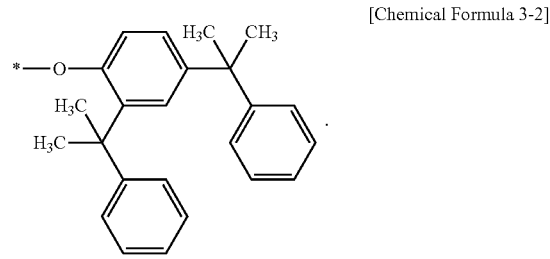 [SMILES: *Oc1ccc(C(C)(C)c2ccccc2)cc1C(C)(C)c1ccccc1]

18. A compound represented by the following Chemical Formula 1:

[Chemical Formula 1]

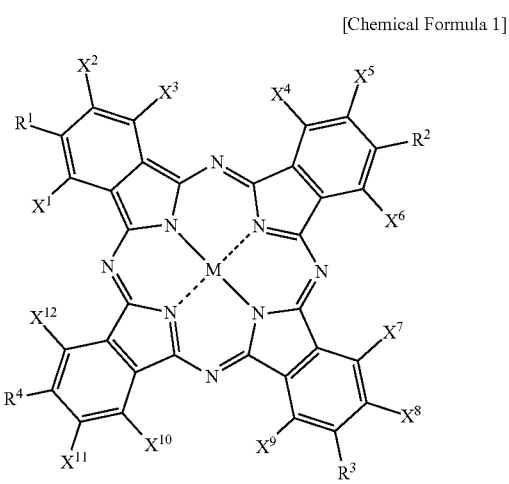

wherein, in Chemical Formula 1,
M is Zn or Cu,
$X^1$ to $X^{12}$ are the same or different and are each independently a hydrogen atom or a halogen atom,
$R^1$ to $R^4$ are the same or different and are each independently a hydrogen atom, a halogen atom, a substituted or unsubstituted C1 to C20 alkyl group, a substituted or unsubstituted C3 to C20 alkoxy group, a substituted or unsubstituted C6 to C20 aryl group, or a substituted or unsubstituted C6 to C20 aryloxy group, provided at least one of $R^1$ to $R^4$ is represented by Chemical Formula 3-2:

[Chemical Formula 3-2]

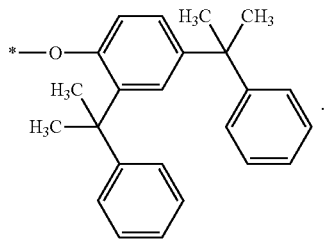

19. The compound of claim 18, wherein the compound represented by Chemical Formula 1 is selected from one or more of Chemical Formula 8, Chemical Formula 12, Chemical Formula 13, Chemical Formula 14, Chemical Formula 15, and Chemical Formula 16:

[Chemical Formula 8]

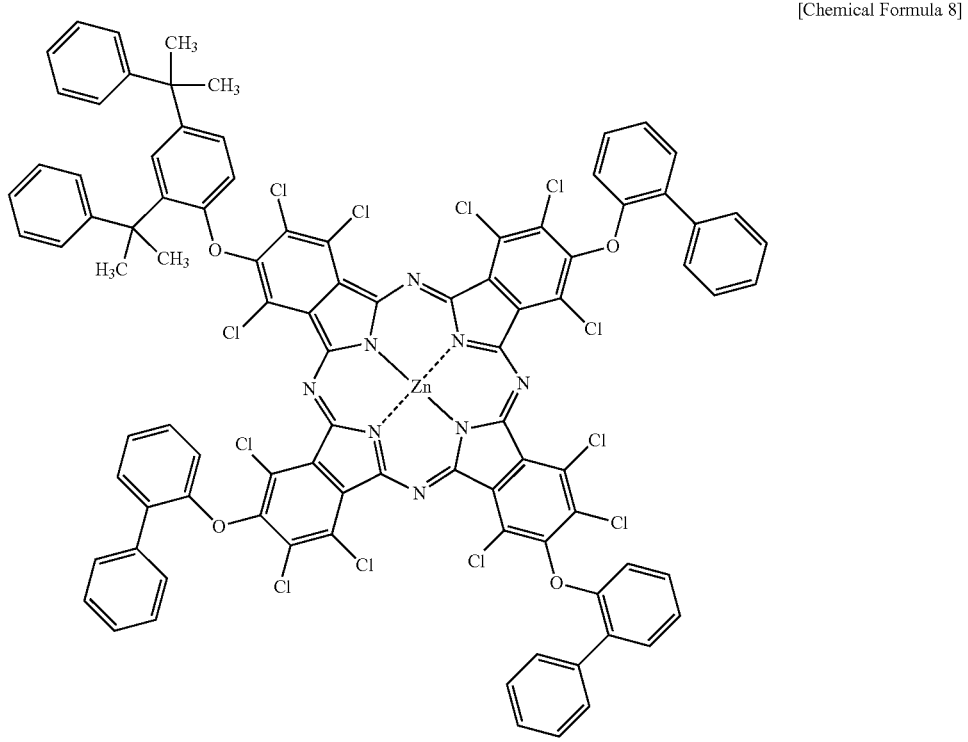

[Chemical Formula 12]
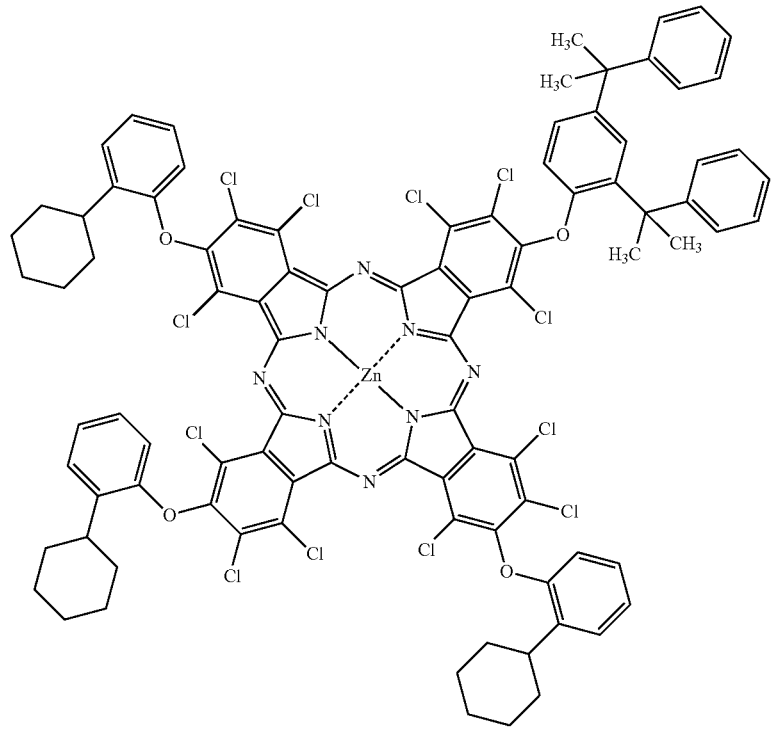
[Chemical Formula 13]
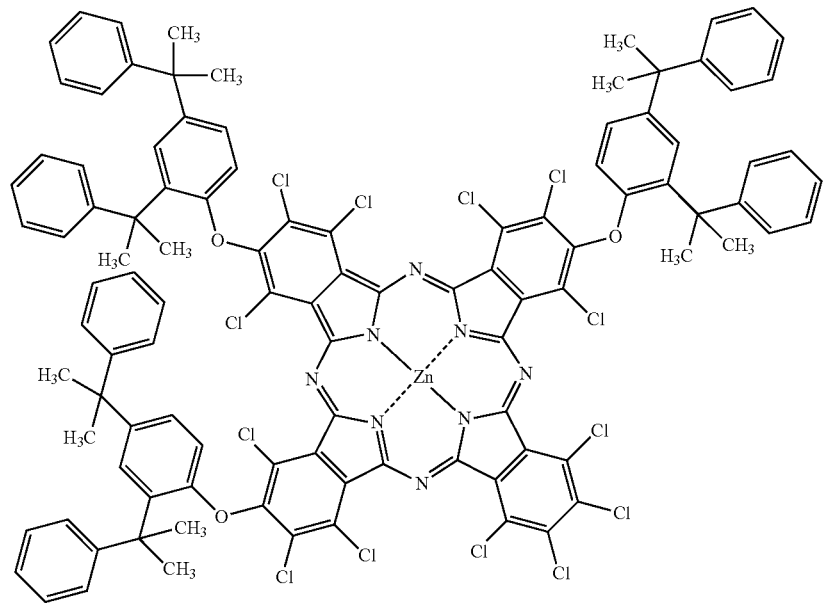

[Chemical Formula 14]
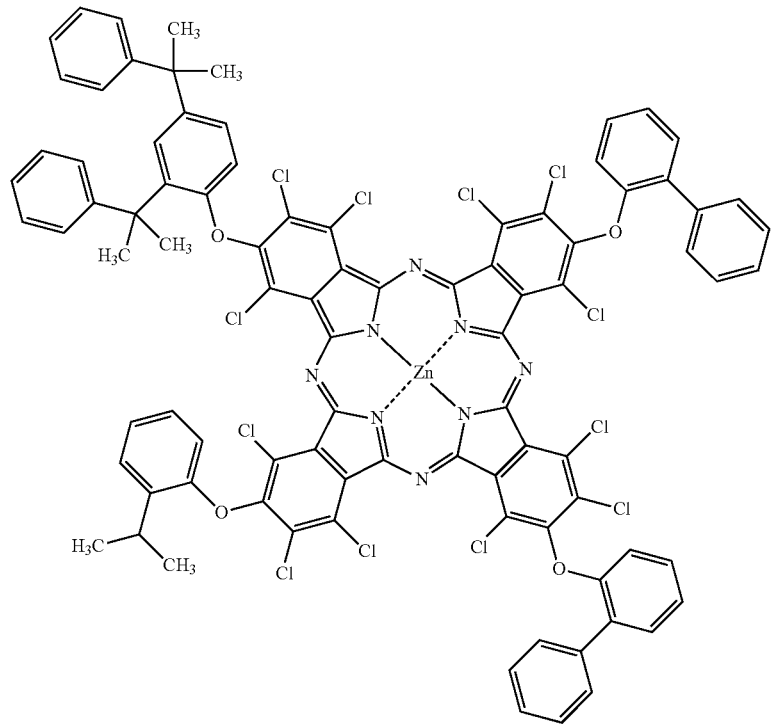
[Chemical Formula 15]
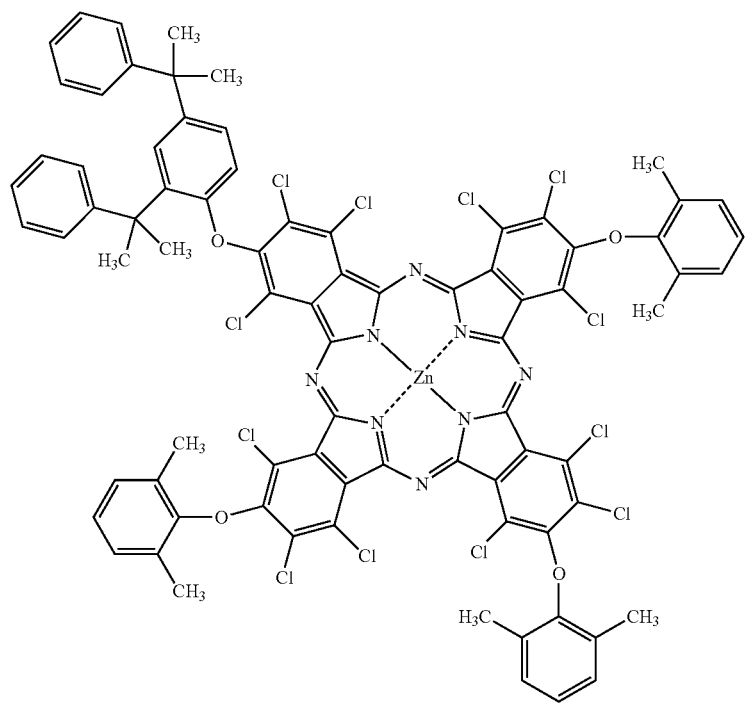

-continued
[Chemical Formula 16]
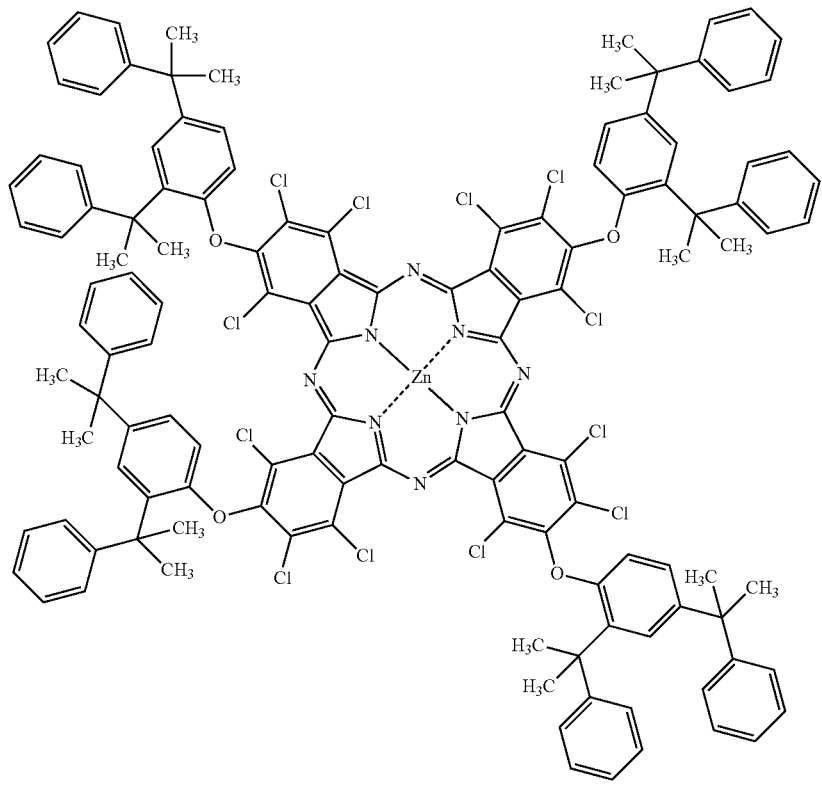
* * * * *

UNITED STATES PATENT AND TRADEMARK OFFICE
CERTIFICATE OF CORRECTION

PATENT NO.         : 9,815,843 B2                    Page 1 of 1
APPLICATION NO.    : 15/266543
DATED              : November 14, 2017
INVENTOR(S)        : Chae Won Pak et al.

It is certified that error appears in the above-identified patent and that said Letters Patent is hereby corrected as shown below:

In the Specification

Column 40, delete Chemical Formula 9 and insert:

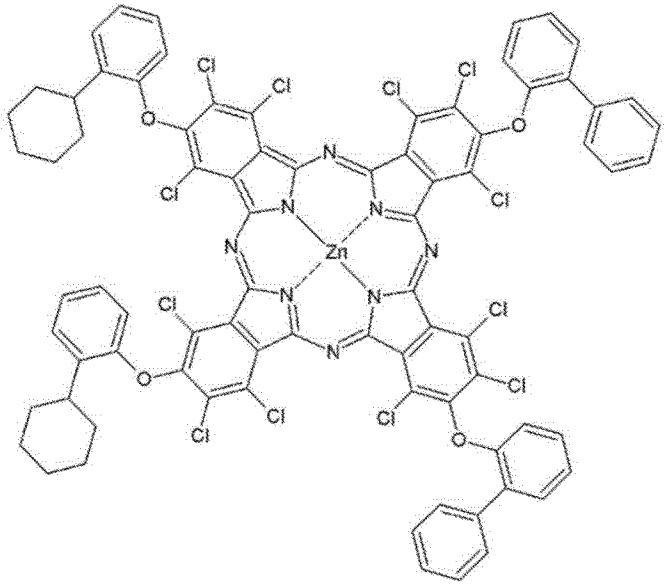

--                                              --

Signed and Sealed this
Second Day of April, 2019

Andrei Iancu
*Director of the United States Patent and Trademark Office*